(12) United States Patent
Krebs et al.

(10) Patent No.: US 10,806,827 B2
(45) Date of Patent: Oct. 20, 2020

(54) CONTROLLED AND TUNABLE PRECIPITATION OF BIOMIMETIC APATITES VIA IN SITU MINERALIZATION OF AN ORGANIC POLYMERIC MATRIX

(71) Applicant: Colorado School of Mines, Golden, CO (US)

(72) Inventors: Melissa Krebs, Englewood, CO (US); Jacqueline Harding, Golden, CO (US)

(73) Assignee: Colorado School of Mines, Golden, CO (US)

(*) Notice: Subject to any disclaimer, the term of this patent is extended or adjusted under 35 U.S.C. 154(b) by 0 days.

(21) Appl. No.: 15/170,630

(22) Filed: Jun. 1, 2016

(65) Prior Publication Data

US 2016/0346429 A1 Dec. 1, 2016

Related U.S. Application Data

(60) Provisional application No. 62/169,330, filed on Jun. 1, 2015.

(51) Int. Cl.

| | |
|---|---|
| *A61L 27/12* | (2006.01) |
| *A61L 27/36* | (2006.01) |
| *A61L 27/54* | (2006.01) |
| *A61L 27/46* | (2006.01) |

(52) U.S. Cl.
CPC ............. *A61L 27/54* (2013.01); *A61L 27/46* (2013.01); *A61L 2430/02* (2013.01); *A61L 2430/12* (2013.01)

(58) Field of Classification Search
CPC ...... A61L 27/46; A61L 27/54; A61L 2430/02; A61L 2430/12
See application file for complete search history.

(56) References Cited

U.S. PATENT DOCUMENTS

| | | | |
|---|---|---|---|
| 2006/0134160 A1 | 6/2006 | Troczynski et al. | |
| 2007/0098799 A1* | 5/2007 | Zhang | A61L 27/46 424/486 |
| 2017/0326272 A1 | 11/2017 | Harding et al. | |

OTHER PUBLICATIONS

Peppas, et al., "Structure and Application of poly(vinyl alcohol) Hydrogels Produced by Conventional Crosslinking or by Freezing / Thawing Methods", Adv. Polymer Sci. 153, 37 (2000). (Year: 2000).*
"chronOS® Bone Void Filler," DePuySynthes, 2014, 8 pages.
"HydroSet Injectable Bone Substitute," brochure, Stryker, 2014, 6 pages.

(Continued)

*Primary Examiner* — Jianfeng Song
(74) *Attorney, Agent, or Firm* — Sheridan Ross P.C.

(57) ABSTRACT

The present invention is directed to a method for the tunable precipitation of apatite induced by a chemical reaction within a polymeric hydrogel, and the product made thereof. The present invention includes a pH dependent pathway for the hydrolysis of DCPD precursor phase. In addition to pH the stoichiometry of the CaP reactants can contribute to the composition of the CaP phase incorporated into the PVA hydrogels. At elevated pH the direct conversion of DCPD to apatite is observed. However, decreasing the reaction pH to 7.4 to mimic physiological conditions results in the inclusion of OCP as a transition step.

18 Claims, 13 Drawing Sheets
(4 of 13 Drawing Sheet(s) Filed in Color)

(56) References Cited

OTHER PUBLICATIONS

"Pro-Dense® Graft-Bone Graft Substitute," Wright, 2015, retrieved from https://web.archive.org/web/*/http://www.wright.com/physicians/prodense/product-overview, 2 pages.

Bleek et al., "New developments in polymer-controlled, bioinspired calcium phosphate mineralization from aqueous solution," Acta Biomaterialia, 2013, vol. 9(5), pp. 6283-6321, 2 pages, abstract only.

Dorozhkin et al., "Biological and Medical Significance of Calcium Phosphates," Angewandte Chemie, 2002, vol. 41(17), pp. 3130-3146, 3 pages, abstract only.

Elliott, "Mineral, synthetic and biological carbonate apatites," Structure and Chemistry of the Apatites and Other Calcium Orthophosphates (book), Elsevier, 1994, pp. 191-304, 1 pages, abstract only.

Harding et al, "Controlled and Tunable Biomimetic Apatite Mineralization of Synthetic Hydrogels," Macromolecular Materials and Engineering, 2016, 3 pages, abstract only.

Kumar et al., "Transformation of modified brushite to hydroxyapatite in aqueous solution: effects of potassium substitution," Biomaterials, 1999, vol. 20(15), pp. 1389-1399, 2 pages, abstract only.

Raynaud et al., "Calcium phosphate apatites with variable Ca/P atomic ratio I. Synthesis, characterisation and thermal stability of powders," Biomaterials, 2002, vol. 23(4), pp. 1065-1072, 1 page, abstract only.

Rezwan et al., "Biodegradable and bioactive porous polymer/inorganic composite scaffolds for bone tissue engineering," Biomaterials, 2006, vol. 27(19), pp. 3413-3431, 1 page, abstract only.

John et al., "A trial to prepare biodegradable collagen-hydroxyapatite composites for bone repair," Journal of Biomaterials Science-Polymer Edition, 2001, vol. 12(6), pp. 689-705, abstract only, 2 pages.

Oonishi et al., "Clinical Application of Hydroxyapatite in Orthopedics," Advances in Calcium Phosphate Biomaterials, Chapter 2, 2014, pp. 19-49.

Schweizer et al., "Polymer-Controlled, Bio-Inspired Calcium Phosphate Mineralization from Aqueous Solution," Macromolecular Bioscience, 2007, vol. 7(9-10), pp. 1085-1099, abstract only, 2 pages.

Surmenev, "review of plasma-assisted methods for calcium phosphate-based coatings fabrication," Surface & Coatings Technology, 2012, vol. 206, pp. 2035-2056.

Yang et al., "Artificial hydroxyapatite film for the conservation of outdoor marble artworks," Materials Letters, 2014, vol. 124, pp. 201-203, abstract only, 2 pages.

Zadpoor, "Relationship between in vitro apatite-forming ability measured using simulated body fluid and in vivo bioactivity of biomaterials," Materials Science and Engineering: C, 2014, vol. 35, pp. 134-143, abstract only, 2 pages.

* cited by examiner

CONTROLLED AND TUNABLE PRECIPITATION OF BIOMIMETIC APATITES VIA IN SITU MINERALIZATION OF AN ORGANIC POLYMERIC MATRIX

CROSS REFERENCE TO RELATED APPLICATIONS

This application claims priority and the benefit under 35 U.S.C. § 119(e) to U.S. Provisional Application Ser. No. 62/169,330, filed on Jun. 1, 2015, which is incorporated by reference in its entirety.

FIELD OF THE INVENTION

The present invention is directed to a method to form a biomimetic apatite within a polymer, the biomimetic apatite within the polymer and methods of use of the apatite in the polymer.

BACKGROUND

Biomineralization is an essential process utilized by numerous organisms in the construction of shells, teeth, and the formation of a skeleton. Repair of damage to mineralized tissues resulting from trauma or genetic defects is a lengthy and inefficient process requiring the use of grafts. Bone is the second most grafted tissue trailing only skin and is used for the reconstruction of large and small defects alike with predominant usage in dental, craniofacial reconstructions, spinal fusions, and to a smaller extent repair of long bone defects. Current best practices for grafts are derived from natural tissues either as autografted or allografted materials. The widespread use of natural tissue for restorative and regenerative procedures is limited due to graft availability, and there are risks associated with harvesting tissue from the patient and risks of rejection with allografts. As an alternative, synthetic graft materials offer the opportunity for supply that can meet the demand and also importantly do not risk rejection associated with the foreign body response.

Apatite is a naturally occurring mineral found in bone and dental tissue. As a true biomaterial synthetic material, apatites are frequently encountered as additives in polymeric materials for use in biological applications to inhibit the foreign body response and promote healing. Synthetic bone graft materials rely on the incorporation of a calcium phosphate (CaP) mineral in an attempt to mimic natural mineralized tissue. Many incorporated CaP phases are synthetically derived with the frequent use of hydroxyapatite (HA) and tricalcium phosphate (TCP). The significant drawback of these minerals is that they are often difficult for biological systems to resorb, inhibiting the construction of healthy tissue. Thus, these materials cannot be incorporated to mimic the necessary structural properties of bone tissue limiting the use to sites which are not intrinsic to the stability of the bony structure.

CaP, particularly HA, is frequently used in the construction of biomaterials due to their well-established bioactive and biointegrative properties, which are attributed to the close resemblance of natural bone mineral. Common applications include coatings on implantable prostheses to promote integration and also for materials that promote the repair of dental or bone defects. However, complications are frequently encountered in trying to use HA, including the low resorbability of synthetic HA and its inability to mimic the important physical and chemical properties of natural apatite.

SUMMARY

In the United States alone, there are approximately 200 million bone graft procedures performed annually, and this number is just a small fraction compared to the need for CaP based materials in dental applications where the implant market is expected to exceed $6 billion in the next 3 years. An alternative to traditional formulations of CaP based synthetic grafts is the controlled precipitation of biological apatites within the polymeric support substrate as set forth herein.

The present invention provides a method to tailor materials to mimic the natural composition of bone and dental tissue to serve in the repair and potential regeneration to healthy tissue. Advantageously, the present invention facilitates the conversion of CaP into biomimetic apatite through the manipulation of CaP ratio, temperature, and pH.

Mineralized tissues, particularly the skeleton, are considered to be composite materials formed by the nucleation of CaP polymorphs on a collagen substrate. These CaP polymorphs are sequentially matured, where the initially deposited CaP phase secreted by osteoblasts is amorphous calcium phosphates or dicalcium phosphate dihydrate (DCPD), which under physiological conditions shown in equation (1) is hydrolyzed to intermediate phase octacalcium phosphate (OCP).

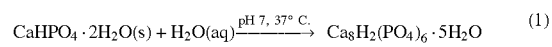

$$CaHPO_4 \cdot 2H_2O(s) + H_2O(aq) \xrightarrow{pH\ 7,\ 37°\ C.} Ca_8H_2(PO_4)_6 \cdot 5H_2O \quad (1)$$

A second hydrolysis reaction of OCP equation (2) results in the formation of mature apatite, where the chemical composition of apatite is known to vary between bone and teeth based on the substitution of the apatite lattice with carbonate or fluoride ions, respectively (Table 1). Table 1 includes composition and structural parameters of synthetic and natural CaP mineral phases.

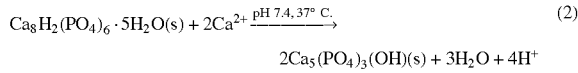

$$Ca_8H_2(PO_4)_6 \cdot 5H_2O(s) + 2Ca^{2+} \xrightarrow{pH\ 7.4,\ 37°\ C.} 2Ca_5(PO_4)_3(OH)(s) + 3H_2O + 4H^+ \quad (2)$$

TABLE 1

| CaP Polymorph | Formula | Ca/P (ratio) | Formation pH | Solubility (pK$_{sp}$) |
|---|---|---|---|---|
| HA | Ca$_6$(PO$_4$)$_5$(OH) | 1.67 | >9 | 116.8 |
| DCPD | CaHPO$_4$ 2H$_2$O | 1 | 3-5 | 6.59 |
| OCP | Ca$_8$H$_2$(PO$_4$)$_6$ 5H$_2$O | 1.33 | 5-7.4 | 68.6 |
| Carbonated Apatite | Ca$_{10}$(PO$_4$)$_6$CO$_3$ | 1.71 | 7.4 | |
| Bone | Ca$_5$(PO$_4$)$_3$(OH)$_{x-y}$(CO$_3$)$_y$ | 1.63 | | |
| Enamel | Ca$_5$(PO$_4$)$_3$(OH)$_{x-y-z}$(CO$_3$)$_y$F$_z$ | | | |

TABLE 1-continued

| CaP Polymorph | Formula | Ca/P (ratio) | Formation pH | Solubility ($pK_{sp}$) |
|---|---|---|---|---|
| Tricalcium phosphate | $Ca_3(PO_4)_2$ | 1.5 | 5.9 | |
| Bone (Apatite-$CO_2$) | $Ca(PO4)(CO3)$ | 1.71 | 7.4 | 52.14 |
| Enamel (Fluorapatite) | $Ca(PO4)(F)$ | 1.67 | 7.4 | 57.19 |

As a result, the use of synthetic HA as a structural prototype for naturally mineralized apatites has been emphasized in the research and development of synthetic bone grafts. The use of HA materials has been shown to improve integration with the native tissue by minimizing the foreign body response and by creating an osteoconductive surface. However, the preparation of HA requires reaction temperatures in excess of 900° C. and alkaline pH resulting in a highly crystalline CaP polymorph with a solubility product that is doubled compared to biosynthesized apatite, shown in Table 1 as bone and enamel. The solubility of the mineral has an influence on the rate of resorption by cellular processes in the body, which impacts tissue regeneration. The present invention provides a method for the controlled mineralization of synthetic polymer grafts utilizing a bioinspired approach. Polymer-supported precipitation of biomimetic CaP polymorphs has been the subject of extensive research in recent years based on its potential for directing the growth of CaP under physiological conditions. Polymer-assisted CaP growth can be split into categories, including: 1) aqueous solutions with solubilized polymers, surfactants or even proteins; and 2) direct nucleation onto an insoluble polymeric substrate. Solution assisted growth process are shown to influence the resulting CaP polymorph phase based on the chemical functionalities associated with the polymeric substrate. The use of hydrogels as mineralization mediums is of the most interest since it most closely resembles the gel-like matrix of natural bone. The most frequently explored approach is the biomimetic mineralization of polymeric surfaces by immersion in simulated body fluid (SBF) solutions at physiological pH and temperature. The nucleation of apatite onto polymeric surfaces in SBF is a well-known process and is widely considered to be a primary indicator for predicting in vivo bioactivity. However, the use of SBF immersion for the preparation of synthetic grafts is limited due to slow rates of mineralization and the inability to tune the composition and morphology of the resulting mineral phase. Surface deposition of apatite using a layer by layer growth approach is regularly explored, however once again control over the resulting crystal composition and morphology was not successful. A popular alternative approach to mineralizing hydrogels is a double diffusion technique where CaP is precipitated within the polymer when diffused Ca' and phosphate ions interact in a polymer solution. Again, significant hurdles exist with this approach, including the ability to control the dispersion of the mineral throughout the matrix and the resulting mineral phase. Despite extensive investigations of methods for the in situ mineralization of hydrogels, a method for the controlled and tunable growth of biomimetic CaPs in hydrogels has yet to be developed.

The present invention represents a systematic approach to the controlled in situ precipitation of biomimetic CaPs within a polymeric matrix. The integration of the mineral phase into the polymeric carrier phase has historically involved the preparation of the materials separately, due to the rather intense reaction conditions needed for synthetic apatite, followed by dispersion of the solid into the matrix. However, the development of biological apatites are known to occur under comparatively mild conditions of biological temperature (about 37° C.) and pH of about 7.4. A frequent approach to the deposition of biomimetic CaP is through the immersion of the material into SBF ion solution for extended duration. While mineralization is known to occur using this process, the duration and lack of control over the mineral composition or morphology is a limiting factor. Through the manipulation of three key reactions variables during maturation, including temperature, pH, and calcium:phosphate stoichiometry, the mineral phase and morphology of apatite minerals can be controlled within the polymeric matrix.

The controlled precipitation of the natural CaP phases is conducted by directly adding solutions of calcium and phosphate salts to an aqueous polymer solution. The direct addition of each ion to the polymer allows for stoichiometric control of the reactants. Upon addition, the immediate reaction of the calcium and phosphate ions occurs forming metastable CaP, Dicalcium Phosphate Dihydrate (DCPD). Through the subjection of polymer-CaP material to hydrolysis conditions by immersion in a solution of increased pH (7-9) and reaction temperature (37° C.), the maturation of the crystal phase can be induced into biomimetic apatite.

In one embodiment, the present invention can incorporate a mineral phase adhered to the polymer. The mineral can be homogetic in the graft. This approach allows for tuning of the chemical composition to resemble biological apatites found in bone or dental tissue. The precipitation of the proper mineral phase can be initiated prior to biological incorporation or slowly matured within the biological environment. The diversity of this method lies in the polymeric template or precursor used in construction of the material allowing for preparation of injectable gels or robust implantable grafts. A material produced with this method can be successfully implemented in the construction of biomimetic bone or dental grafts and even applied as coating to existing biomedical devices.

The present invention can be used on existing medical devices as nonfouling coatings or as materials in the construction of synthetic bone substitutes. CaP based coatings are currently used on metallic implants including replacement hips and knee joints. Synthetic bone substitutes are frequent used as bone void fillers to treat bony defect that are created either surgically or as a result of traumatic injury. These implants are frequent used in spinal fusion surgeries for stabilizing vertebras, fracture treatment of long and flat bones, and as dental grafts for the restoration of lost jaw bone. In spinal fusion applications alone between 2008-2009, there was a 137% increase in the number of procedures from 174,223 to 413,171 thereby increasing the market value from $14.3 billion to $33.9 billion. This value is projected to increase as the population continues to age. Current synthetic bone graft materials exhibit only a moderate degree of success and are not considered suitable substitutes to autografts or allografts. Synthetic grafts are designed to mimic the composition of natural bone tissue through the incorporation of a CaP mineral phase into the polymeric scaffold. Synthetic HA and TCP are two frequently utilized CaP phases, however the limitation of success in bone grafts is attributed to the fact that these CaP phases do not in fact mimic the composition of biological apatites and there is a lack of homogeneity of the dispersed mineral throughout the synthetic graft. The present invention will solve this problem by allowing for the controlled precipitation of biomimetic apatites within the polymeric substrate. The use of biomimetic apatites will facilitate the necessary resorption of the mineral necessary for the reconstruction of healthy tissue. Furthermore, the direct nucleation of CaP onto the polymeric substrate will facilitate a homogenous distribution of the mineral phase, which correlates to how natural bone tissue is formed. Through the control of the mineral phase and deposition location, truly biomimetic grafts can be developed that are suitable for both dental and bone reconstruction applications as well as potential use in previously inaccessible weight bearing applications. The advantage to this approach is that current commercial manufacturing process will not require significant modification to achieve this result, but rather the only requirement will be an additional maturation step to precipitate the desired mineral phase.

Applications for materials made from the present invention include the repair of damaged mineralized tissues including bone and teeth. A less obvious area of application is in the development of antifouling coating on biomedical devices. Apatite is recognized as a true biomaterial and as a result does not result in foreign body responses when utilized in a biomedical device. Foreign body response accounts for high rates of device fouling which ultimately compromises utility. Therefore, in addition to targeting the synthetic bone graft market, this technology can be applied to a wide spectrum of implantable biomedical devices as coatings to extend their duration of use and compatibility within body. Coating is a field which is extensive and a highly lucrative market.

The present intention is a method for the tunable precipitation of apatite induced by a chemical reaction within a polymeric hydrogel. A pH dependent pathway for the hydrolysis of DCPD precursor phase is contemplated. In addition to pH, the stoichiometry of the CaP reactants contributes to the composition of the CaP phase incorporated into the PVA hydrogels. At elevated pH the direct conversion of DCPD to apatite is observed. However, decreasing the reaction pH to 7.4 to mimic physiological conditions results in the inclusion of OCP as a transition step. The reaction mechanism of in situ apatite synthesis at pH 7.4 mimics the reaction mechanism proposed for biological tissues. Furthermore, the reaction conditions were found to influence the crystalline morphology of the apatite product. Mimicking biological apatite precipitation reactions plate-like apatite was formed throughout the polymeric hydrogel and is reminiscent of naturally mineralized tissues including bone and teeth. The capacity to develop a biomimetic material is a considerable advantage for the off the shelf availability of graft materials for use in clinical settings.

An aspect of the invention is a method to form a biological apatite hydrogel composite. The method includes preparing a polymer hydrogel. The hydrogel is mixed with a calcium source, and a phosphate source to produce a slurry. The polymer in the slurry is crosslinked to produce a polymer comprising a DCPD in the hydrogel. The polymer comprising the DCPD in the hydrogel is soaked in an aqueous solution to produce the biological apatite hydrogel composite.

An aspect of the invention is a method to form a biological apatite precursor within a hydrogel. The method includes preparing a polymer hydrogel. A calcium source and a phosphate source are provided to the hydrogel to produce the biological apatite precursor within the hydrogel.

An aspect of the invention is a biological apatite hydrogel composite. The apatite includes a polymer, and calcium phosphate. The calcium phosphate is dispersed in the polymer to form the biological apatite hydrogel composite.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
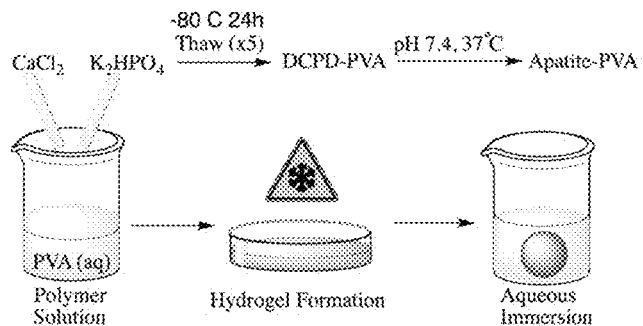
FIG. 1A illustrates the preparation of a mineralized hydrogel composite material.

The present invention is directed to a method to form a biomimetic apatite in a hydrogel, the biomimetic apatite in a hydrogel, and methods of use of the apatite in a hydrogel.

An aspect of the invention is a method to form a biological apatite. The method includes preparing a polymer hydrogel. The hydrogel is mixed with a calcium source and a phosphate source to produce a slurry. The slurry is crosslinked to produce a polymer comprising an apatite. The polymer is then soaked in an aqueous solution to produce the biological apatite.

The polymer hydrogel can be a water soluble hydrophilic polymers functionalized with hydroxyl, carboxyl, phosphate, thiol, amino acid groups, or combinations thereof. Other suitable polymer hydrogels include, but are not limited to, polyvinyl alcohol, a collagen, a methyl acrylate, a polyethylene glycol, an alginate, dextran, hyaluronic acid, a gelatin, a chitosan, a cellulose, or combinations thereof. The polymer can be prepared by mixing the polymer with water. The water can be distilled, deionized, or tap water. One skilled in the art would understand that ions present in the water can be incorporated into the polymer. Thus, it can be advantageous to use deionized water to prevent the incorporation of ions into the polymer sourced from the water. Between about 2 to about 20 wt. % of the polymer can be added to water to form the hydrogel, in some embodiments about 10 wt. % of polymer can be added to the water.

The calcium source can be soluble. Suitable calcium sources include, but are not limited to, calcium chloride, calcium nitrate, calcium carbonate, calcium fluoride, and combinations thereof. The phosphate source can be a dibasic phosphate compound. Suitable dibasic phosphate compounds include but are not limited to, dipotassium phosphate, ammonium phosphate, phosphoric acid and combinations thereof. The phosphate source can be chosen to reduce or eliminate the incorporation of undesirable ions into the biological apatite. For example, ammonia phosphate does not incorporate ions into the biological apatite product sourced from the ammonia phosphate. Sodium phosphate would provide sodium to the biological apatite. A ratio of the calcium source to the phosphate source can be between about 1:0.5 to 1:2, in some embodiments about 1:1.67. The calcium: phosphate stoichiometry can be controlled based on the ratio of calcium and phosphate. Furthermore, the apatite can be stoichimetrically balanced, or not balanced, as desired.

The temperature during mixing can be between about 20° C. and about 40° C., in some embodiments about 37° C. The pH of the slurry can be between about 3.5 and about 5. The pH can be adjusted to this range with a strong acid, for example, hydrochloric acid, nitric acid, sulphuric acid, and combinations thereof. The strong acid can be selected so that an ion is not incorporated into the biological apatite sourced from the acid.

The polymer can be crosslinked using several different methods that are dependent upon the polymer. In some embodiments for some polymers, the polymer can be crosslinked by thermal cycling the slurry. Any temperature can be used in the thermal cycle that results in the polymer freezing, then thawing. While microstructures of the material can result (which can be dependent upon the temperatures that the polymer is exposed to during thermal cycling), the resulting polymer can result in a crosslinked polymer. In some embodiments, the slurry can be thermal cycled at temperatures between about −80° C. and about 20° C. at least four cycles to form a biological apatite precursor. The polymer can be held at the temperature (cold or warm temperature) for between about 4 hours to about 24 hours. In this embodiment, the slurry can be frozen at about −80° C., and thawed at room temperature (approximately 20° C.). Other suitable thermal cycling ranges include, but are not limited to about −20° C. to about 20° C. Polymers that can be crosslinked by thermal cycling include, but are not limited to, polyvinyl alcohol. An additional method to crosslink collagen can be by subjecting the collagen to a dehydrothermal treatment, which is a process by which the collagen is frozen (at a temperature between about −200° C. and about −20° C.), immediately lyophilize for between about 24 hours and about 72 hours, in some embodiments about 48 hours, then dehydrothermally crosslinked in a vacuum oven at between about 85° C. and about 125° C., in some embodiments about 105° C., at a pressure of between about 20 inHg and about 35 inHg, in some embodiments about 29 inHg, for between about 12 hours to about 48 hours, in some embodiments about 24 hours. While additional cycles can be used, one cycle can be sufficient in the dehydrothermal treatment. An advantage of crosslinking the polymer by thermal cycling can be that no ion sourced from a crosslinking material can be incorporated into the apatite.

In some embodiments for some polymers, the polymer can be crosslinked using a crosslinking agent selected from the group consisting of glutaraldehyde, or 1-ethyl-3-(3-dimethylaminopropyl)carbodiimide hydrochloride (EDC). Polymers that can be crosslinked using a crosslinking agent include, but are not limited to, polyvinyl alcohol, a collagen, a methyl acrylate, a polyethylene glycol, an alginate, dextran, hyaluronic acid, a gelatin, a chitosan, a cellulose, or combinations thereof. In some embodiments, a polymer can be crosslinked using photocrosslinking. Photocrosslinking can be particularly useful for producing methacrylate polymer. Photocrosslinking can comprise providing an UV light on the polymer. Advantageously, photocrosslinking is a non-chemical method, and therefore would not incorporate an ion into the polymer. In some embodiments, the polymer can be ionically crosslinked (e.g. crosslinking an alginate with calcium).

The aqueous solution can be at a pH between about 4 and about 11 and soaked for between about 24 to about 168 hours, in some embodiments about 72 hours, at a temperature between about 30° C. to about 70° C., in some embodiments about 37° C. In some embodiments, the temperature can be about 37° C. to mimic physiological conditions. The mineral phase can withstand temperatures in excess of about 1000° C., and are typically be limited by the polymer stability. An organic polymer can typically withstand temperatures up to about 400° C. before undergoing complete thermally induced decomposition. Furthermore, the aqueous reaction can occur in a sealed or unsealed container. If the reaction occurs in an unsealed container, the reaction temperatures cannot exceed boiling point of water, which is approximately 100° C. If the reaction occurs in a sealed container, then the temperature can exceed about 100° C., up to decomposition point of polymer of about 400° C.

The pH can affect the mineral phase of the apatite. When the aqueous solution is at a pH between about 7.4-11, a mineral phase biological apatite can be formed. When the aqueous solution is at a pH of between about 6.5 to about 7.4, the mineral phase biological apatite formed can include OCP. OCP can be an intermediate phase, that can be converted to other materials such as TCP, enamel, bone, apatite, with further processing. Furthermore, OCP can mature into apatite after approximately 2 days. OCP can tune the mineral transformation to mimic biological mineralization pathways.

The aqueous solution can further comprise an additive source of material for a particular end use. For example, the aqueous solution can comprise between about 0.0042-0.1 M of an additive source can be included in the aqueous solution such that the biological apatite comprises ions. Suitable additive sources include bicarbonate, fluoride, sodium, potassium, chloride, magnesium, citrate ions and combination thereof. The resulting ions in the biological apatite can be biologically available in use. For example, fluorine can also be added to the biological apatite. Fluorine can be useful in dental applications. Between about 0.01 M and about 0.1 M of a fluorine additive can be included in the aqueous solution. Suitable fluorine additives include, but are not limited to, fluorine salts, which can be prepared from alkali and/or alkaline metal ions, including but not limited to sodium fluoride, calcium fluoride, potassium fluoride, combinations thereof, or acids such as hydrofluoric acid and combinations thereof. Other suitable additives include sodium, magnesium, potassium, chlorine, iodine, lithium, citrate ions, and combinations thereof. The aqueous solution can be deionized water, phosphate buffer, hepes buffer, goods buffers (which can be tunes to an appropriate or desired pH range), tris buffer, SBF, or the like. The type of aqueous solution can affect the final mineral property. For example, when a tris buffer is used as the aqueous solution (without any additives), the resulting apatite is not substituted. When SBF is used, the resulting apatite can be substituted with the ionic component of the solution, which can be sodium, magnesium, potassium, chlorine, or combinations thereof. The final composition comprising the ions, for example calcium or phosphate ions, can result in larger crystals.

The biological apatite can further include an enhancer. The enhancer can be a protein, a cell, a drug, an antibody, a growth factor, a cell, and combinations thereof. Between about 0.001 mg and about 1.0 mg grams of the enhancer can be added to the biological apatite. The enhancers can be added to the biological apatite by soaking the mineralized matrices in the enhancer, or by seeding the enhancer by putting a concentrated cell suspension on top of the matrix and allowing the cells to adhere and proliferate on the matrix. Combinations of these method can also be used. The biological apatite can also have at least one property selected from the group consisting of bioactive, osteoinductive, osteoconductive and combinations thereof.

An aspect of the invention is a biological apatite hydrogel. The polymer hydrogel comprises a calcium phosphate salt, prepared by combining calcium and phosphate. The calcium phosphate salt can be randomly distributed in the polymer hydrogel.

The polymer hydrogel can be a water soluble hydrophilic polymers functionalized with hydroxyl, carboxyl, phosphate, thiol, amino acid groups, or combinations thereof. Other suitable polymer hydrogels include, but are not limited to, polyvinyl alcohol, a collagen, a methyl acrylate, a polyethylene glycol, an alginate, dextran, hyaluronic acid, a gelatin, a chitosan, a cellulose, or combinations thereof.

The calcium source can be soluble. Suitable calcium sources include, but are not limited to, calcium chloride, calcium nitrate, calcium carbonate, calcium fluoride, and combinations thereof. The phosphate source can be a dibasic phosphate compound. Suitable dibasic phosphate compounds include but are not limited to, dipotassium phosphate, ammonium phosphate, phosphoric acid and combinations thereof. The phosphate source can be chosen to reduce or eliminate the incorporation of undesirable ions into the biological apatite. For example, ammonia phosphate does not incorporate ions into the biological apatite product sourced from the ammonia phosphate. Sodium phosphate would provide sodium to the biological apatite. A ratio of the calcium source to the phosphate source can be between about 1:0.5 to 1:2, in some embodiments about 1:1.67. The calcium: phosphate stoichiometry can be controlled based on the ratio of calcium and phosphate. Furthermore, the apatite can be stoichimetrically balanced, or not balanced, as desired.

In some embodiments, the polymer can be ionically crosslinked (e.g. crosslinking an alginate with calcium).

The pH during processing can affect the mineral phase of the apatite. When the aqueous solution is at a pH between about 7.4-11, a mineral phase biological apatite can be formed. When the aqueous solution is at a pH of between about 6.5 to about 7.4, the mineral phase biological apatite formed can include OCP. OCP can be an intermediate phase, that can be converted to other materials such as TCP, enamel, bone, apatite, with further processing. Furthermore, OCP can mature into apatite after approximately 2 days. OCP can tune the mineral transformation to mimic biological mineralization pathways.

The apatite can further include an additive source of material for a particular end use. For example, the biological apatite includes ions. Suitable additive include bicarbonate, fluoride, sodium, potassium, chloride, magnesium, citrate ions and combination thereof. The resulting ions in the biological apatite can be biologically available in use. For example, fluorine can also be added to the biological apatite. Fluorine can be useful in dental applications. Suitable fluorine additives include, but are not limited to, fluorine salts, which can be prepared from alkali and/or alkaline metal ions, including but not limited to sodium fluoride, calcium fluoride, potassium fluoride, combinations thereof, or acids such as hydrofluoric acid and combinations thereof. Other suitable additives include sodium, magnesium, potassium, chlorine, iodine, lithium, citrate ions, and combinations thereof. The aqueous solution used during processing can be deionized water, phosphate buffer, hepes buffer, goods buffers (which can be tunes to an appropriate or desired pH range), tris buffer, SBF, or the like. The type of aqueous solution can affect the final mineral property. For example, when a tris buffer is used as the aqueous solution (without any additives), the resulting apatite is not substituted. When SBF is used, the resulting apatite can be substituted with the ionic component of the solution, which can be sodium, magnesium, potassium, chlorine, or combinations thereof. The final composition comprising the ions, for example calcium or phosphate ions, can result in larger crystals.

The biological apatite can further include an enhancer. The enhancer can be a protein, a cell, a drug, an antibody, a growth factor, a cell, and combinations thereof. Between about 0.001 mg and about 1.0 mg grams of the enhancer can be added to the biological apatite. The enhancers can be added to the biological apatite by soaking the mineralized matrices in the enhancer, or by seeding the enhancer by putting a concentrated cell suspension on top of the matrix and allowing the cells to adhere and proliferate on the matrix. Combinations of these method can also be used. The biological apatite can also have at least one property selected from the group consisting of bioactive, osteoinductive, osteoconductive and combinations thereof.

Advantageously, the apatite can be biodegradable or tuned to be bioresorbable.

An aspect of the invention is a method to form a biological apatite precursor. The method includes preparing a polymer hydrogel. The hydrogel is mixed with a calcium source and a phosphate source to produce a slurry. The slurry is crosslinked to produce the precursor.

The polymer hydrogel can be a water soluble hydrophilic polymers functionalized with hydroxyl, carboxyl, phosphate, thiol, amino acid groups, or combinations thereof. Other suitable polymer hydrogels include, but are not limited to, polyvinyl alcohol, a collagen, a methyl acrylate, a polyethylene glycol, an alginate, dextran, hyaluronic acid, a gelatin, a chitosan, a cellulose, or combinations thereof. The polymer can be prepared by mixing the polymer with water. The water can be distilled, deionized, or tap water. One skilled in the art would understand that ions present in the water can be incorporated into the polymer. Thus, it can be advantageous to use deionized water to prevent the incorporation of ions into the polymer sourced from the water. Between about 2 to about 20 wt. % of the polymer can be added to water to form the hydrogel, in some embodiments about 10 wt. % of polymer can be added to the water.

The calcium source can be soluble. Suitable calcium sources include, but are not limited to, calcium chloride, calcium nitrate, calcium carbonate, calcium fluoride, and combinations thereof. The phosphate source can be a dibasic phosphate compound. Suitable dibasic phosphate compounds include but are not limited to, dipotassium phosphate, ammonium phosphate, phosphoric acid and combinations thereof. The phosphate source can be chosen to reduce or eliminate the incorporation of undesirable ions into the biological apatite. For example, ammonia phosphate does not incorporate ions into the biological apatite product sourced from the ammonia phosphate. Sodium phosphate would provide sodium to the biological apatite. A ratio of the calcium source to the phosphate source can be between about 1:0.5 to 1:2, in some embodiments about 1:1.67. The calcium: phosphate stoichiometry can be controlled based on the ratio of calcium and phosphate. Furthermore, the apatite can be stoichimetrically balanced, or not balanced, as desired.

The temperature during mixing can be between about 20° C. and about 40° C., in some embodiments about 37° C. The pH of the slurry can be between about 3.5 and about 5. The pH can be adjusted to this range with a strong acid, for example, hydrochloric acid, nitric acid, sulphuric acid, and combinations thereof. The strong acid can be selected so that an ion is not incorporated into the biological apatite sourced from the acid.

The polymer can be crosslinked using several different methods that are dependent upon the polymer. In some embodiments for some polymers, the polymer can be crosslinked by thermal cycling the slurry. Any temperature can be used in the thermal cycle that results in the polymer freezing, then thawing. While microstructures of the material can result (which can be dependent upon the temperatures that the polymer is exposed to during thermal cycling), the resulting polymer can result in a crosslinked polymer. In some embodiments, the slurry can be thermal cycled at temperatures between about −80° C. and about 20° C. at least four cycles to form a biological apatite precursor. The polymer can be held at the temperature (cold or warm temperature) for between about 4 hours to about 24 hours. In this embodiment, the slurry can be frozen at about −80° C., and thawed at room temperature (approximately 20° C.). Other suitable thermal cycling ranges include, but are not limited to about −20° C. to about 20° C. Polymers that can be crosslinked by thermal cycling include, but are not limited to, polyvinyl alcohol. An additional method to crosslink collagen can be by subjecting the collagen to a dehydrothermal treatment, which is a process by which the collagen is frozen (at a temperature between about −200° C. and about −20° C.), immediately lyophilize for between about 24 hours and about 72 hours, in some embodiments about 48 hours, then dehydrothermally crosslinked in a vacuum oven at between about 85° C. and about 125° C., in some embodiments about 105° C., at a pressure of between about 20 inHg and about 35 inHg, in some embodiments about 29 inHg, for between about 12 hours to about 48 hours, in some embodiments about 24 hours. While additional cycles can be used, one cycle can be sufficient in the dehydrothermal treatment. An advantage of crosslinking the polymer by thermal cycling can be that no ion sourced from a crosslinking material can be incorporated into the apatite.

In some embodiments for some polymers, the polymer can be crosslinked using a crosslinking agent selected from the group consisting of glutaraldehyde, or 1-ethyl-3-(3-dimethylaminopropyl)carbodiimide hydrochloride (EDC). Polymers that can be crosslinked using a crosslinking agent include, but are not limited to, polyvinyl alcohol, a collagen, a methyl acrylate, a polyethylene glycol, an alginate, dextran, hyaluronic acid, a gelatin, a chitosan, a cellulose, or combinations thereof. In some embodiments, a polymer can be crosslinked using photocrosslinking. Photocrosslinking can be particularly useful for producing methacrylate polymer. Photocrosslinking can comprise providing an UV light on the polymer. Advantageously, photocrosslinking is a non-chemical method, and therefore would not incorporate an ion into the polymer. In some embodiments, the polymer can be ionically crosslinked (e.g. crosslinking an alginate with calcium).

The aqueous solution can be at a pH between about 4 and about 11 and soaked for between about 24 to about 168 hours, in some embodiments about 72 hours, at a temperature between about 30° C. to about 70° C., in some embodiments about 37° C. In some embodiments, the temperature can be about 37° C. to mimic physiological conditions. The mineral phase can withstand temperatures in excess of about 1000° C., and are typically be limited by the polymer stability. An organic polymer can typically withstand temperatures up to about 400° C. before undergoing complete thermally induced decomposition. Furthermore, the aqueous reaction can occur in a sealed or unsealed container. If the reaction occurs in an unsealed container, the reaction temperatures cannot exceed boiling point of water, which is approximately 100° C. If the reaction occurs in a sealed container, then the temperature can exceed about 100° C., up to decomposition point of polymer of about 400° C.

The pH can affect the mineral phase of the apatite. When the aqueous solution is at a pH between about 7.4-11, a mineral phase biological apatite can be formed. When the aqueous solution is at a pH of between about 6.5 to about 7.4, the mineral phase biological apatite formed can include OCP. OCP can be an intermediate phase, that can be converted to other materials such as TCP, enamel, bone, apatite, with further processing. Furthermore, OCP can mature into apatite after approximately 2 days. OCP can tune the mineral transformation to mimic biological mineralization pathways.

The aqueous solution can further comprise an additive source of material for a particular end use. For example, the aqueous solution can comprise between about 0.0042-0.1 M of an additive source can be included in the aqueous solution such that the biological apatite comprises ions. Suitable additive sources include bicarbonate, fluoride, sodium, potassium, chloride, magnesium, citrate ions and combination thereof. The resulting ions in the biological apatite can be biologically available in use. For example, fluorine can also be added to the biological apatite. Fluorine can be useful in dental applications. Between about 0.01 M and about 0.1 M of a fluorine additive can be included in the aqueous solution. Suitable fluorine additives include, but are not limited to, fluorine salts, which can be prepared from alkali and/or alkaline metal ions, including but not limited to sodium fluoride, calcium fluoride, potassium fluoride, combinations thereof, or acids such as hydrofluoric acid and combinations thereof. Other suitable additives include sodium, magnesium, potassium, chlorine, iodine, lithium, citrate ions, and combinations thereof. The aqueous solution can be deionized water, phosphate buffer, hepes buffer, goods buffers (which can be tunes to an appropriate or desired pH range), tris buffer, SBF, or the like. The type of aqueous solution can affect the final mineral property. For example, when a tris buffer is used as the aqueous solution (without any additives), the resulting apatite is not substituted. When SBF is used, the resulting apatite can be substituted with the ionic component of the solution, which can be sodium, magnesium, potassium, chlorine, or combinations thereof. The final composition comprising the ions, for example calcium or phosphate ions, can result in larger crystals.

The biological apatite can further include an enhancer. The enhancer can be a protein, a cell, a drug, an antibody, a growth factor, a cell, and combinations thereof. Between about 0.001 mg and about 1.0 mg grams of the enhancer can be added to the biological apatite. The enhancers can be added to the biological apatite by soaking the mineralized matrices in the enhancer, or by seeding the enhancer by putting a concentrated cell suspension on top of the matrix and allowing the cells to adhere and proliferate on the matrix. Combinations of these method can also be used. The biological apatite can also have at least one property selected from the group consisting of bioactive, osteoinductive, osteoconductive and combinations thereof.

An aspect of the invention is a biological apatite precursor. The precursor can be tuned for a particular application. The precursor comprises calcium and phosphate in a hydrogel. The hydrogel is a crosslinked polymer.

The pH during processing can affect the mineral phase of the apatite. When the aqueous solution is at a pH between about 7.4-11, a mineral phase biological apatite can be formed. When the aqueous solution is at a pH of between about 6.5 to about 7.4, the mineral phase biological apatite formed can include OCP. OCP can be an intermediate phase, that can be converted to other materials such as TCP, enamel, bone, apatite, with further processing. Furthermore, OCP can mature into apatite after approximately 2 days. OCP can tune the mineral transformation to mimic biological mineralization pathways.

The polymer hydrogel can be a water soluble hydrophilic polymers functionalized with hydroxyl, carboxyl, phosphate, thiol, amino acid groups, or combinations thereof. Other suitable polymer hydrogels include, but are not limited to, polyvinyl alcohol, a collagen, a methyl acrylate, a polyethylene glycol, an alginate, dextran, hyaluronic acid, a gelatin, a chitosan, a cellulose, or combinations thereof. The polymer can be prepared by mixing the polymer with water. The water can be distilled, deionized, or tap water. One skilled in the art would understand that ions present in the water can be incorporated into the polymer. Thus, it can be advantageous to use deionized water to prevent the incorporation of ions into the polymer sourced from the water. Between about 2 to about 20 wt. % of the polymer can be added to water to form the hydrogel, in some embodiments about 10 wt. % of polymer can be added to the water.

The calcium source can be soluble. Suitable calcium sources include, but are not limited to, calcium chloride, calcium nitrate, calcium carbonate, calcium fluoride, and combinations thereof. The phosphate source can be a dibasic phosphate compound. Suitable dibasic phosphate compounds include but are not limited to, dipotassium phosphate, ammonium phosphate, phosphoric acid and combinations thereof. The phosphate source can be chosen to reduce or eliminate the incorporation of undesirable ions into the biological apatite. For example, ammonia phosphate does not incorporate ions into the biological apatite product sourced from the ammonia phosphate. Sodium phosphate would provide sodium to the biological apatite. A ratio of the calcium source to the phosphate source can be between about 1:0.5 to 1:2, in some embodiments about 1:1.67. The calcium: phosphate stoichiometry can be controlled based on the ratio of calcium and phosphate. Furthermore, the apatite can be stoichimetrically balanced, or not balanced, as desired.

The temperature during mixing can be between about 20° C. and about 40° C., in some embodiments about 37° C. The pH of the slurry can be between about 3.5 and about 5. The pH can be adjusted to this range with a strong acid, for example, hydrochloric acid, nitric acid, sulphuric acid, and combinations thereof. The strong acid can be selected so that an ion is not incorporated into the biological apatite sourced from the acid.

The polymer can be crosslinked using several different methods that are dependent upon the polymer. In some embodiments for some polymers, the polymer can be crosslinked by thermal cycling the slurry. Any temperature can be used in the thermal cycle that results in the polymer freezing, then thawing. While microstructures of the material can result (which can be dependent upon the temperatures that the polymer is exposed to during thermal cycling), the resulting polymer can result in a crosslinked polymer. In some embodiments, the slurry can be thermal cycled at temperatures between about −80° C. and about 20° C. at least four cycles to form a biological apatite precursor. The polymer can be held at the temperature (cold or warm temperature) for between about 4 hours to about 24 hours. In this embodiment, the slurry can be frozen at about −80° C., and thawed at room temperature (approximately 20° C.). Other suitable thermal cycling ranges include, but are not limited to about −20° C. to about 20° C. Polymers that can be crosslinked by thermal cycling include, but are not limited to, polyvinyl alcohol. An additional method to crosslink collagen can be by subjecting the collagen to a dehydrothermal treatment, which is a process by which the collagen is frozen (at a temperature between about −200° C. and about −20° C.), immediately lyophilize for between about 24 hours and about 72 hours, in some embodiments about 48 hours, then dehydrothermally crosslinked in a vacuum oven at between about 85° C. and about 125° C., in some embodiments about 105° C., at a pressure of between about 20 inHg and about 35 inHg, in some embodiments about 29 inHg, for between about 12 hours to about 48 hours, in some embodiments about 24 hours. While additional cycles can be used, one cycle can be sufficient in the dehydrothermal treatment. An advantage of crosslinking the polymer by thermal cycling can be that no ion sourced from a crosslinking material can be incorporated into the apatite.

In some embodiments for some polymers, the polymer can be crosslinked using a crosslinking agent selected from the group consisting of glutaraldehyde, or 1-ethyl-3-(3-dimethylaminopropyl)carbodiimide hydrochloride (EDC). Polymers that can be crosslinked using a crosslinking agent include, but are not limited to, polyvinyl alcohol, a collagen, a methyl acrylate, a polyethylene glycol, an alginate, dextran, hyaluronic acid, a gelatin, a chitosan, a cellulose, or combinations thereof. In some embodiments, a polymer can be crosslinked using photocrosslinking. Photocrosslinking can be particularly useful for producing methacrylate polymer. Photocrosslinking can comprise providing an UV light on the polymer. Advantageously, photocrosslinking is a non-chemical method, and therefore would not incorporate an ion into the polymer. In some embodiments, the polymer can be ionically crosslinked (e.g. crosslinking an alginate with calcium).

The aqueous solution can be at a pH between about 4 and about 11 and soaked for between about 24 to about 168 hours, in some embodiments about 72 hours, at a temperature between about 30° C. to about 70° C., in some embodiments about 37° C. In some embodiments, the temperature can be about 37° C. to mimic physiological conditions. The mineral phase can withstand temperatures in excess of about 1000° C., and are typically be limited by the polymer stability. An organic polymer can typically withstand temperatures up to about 400° C. before undergoing complete thermally induced decomposition. Furthermore, the aqueous reaction can occur in a sealed or unsealed container. If the reaction occurs in an unsealed container, the reaction temperatures cannot exceed boiling point of water, which is approximately 100° C. If the reaction occurs in a sealed container, then the temperature can exceed about 100° C., up to decomposition point of polymer of about 400° C.

The pH can affect the mineral phase of the apatite. When the aqueous solution is at a pH between about 7.4-11, a mineral phase biological apatite can be formed. When the aqueous solution is at a pH of between about 6.5 to about 7.4, the mineral phase biological apatite formed can include OCP. OCP can be an intermediate phase, that can be converted to other materials such as TCP, enamel, bone, apatite, with further processing. Furthermore, OCP can mature into apatite after approximately 2 days. OCP can tune the mineral transformation to mimic biological mineralization pathways.

The aqueous solution can further comprise an additive source of material for a particular end use. For example, the aqueous solution can comprise between about 0.0042-0.1 M of an additive source can be included in the aqueous solution such that the biological apatite comprises ions. Suitable additive sources include bicarbonate, fluoride, sodium, potassium, chloride, magnesium, citrate ions and combination thereof. The resulting ions in the biological apatite can be biologically available in use. For example, fluorine can also be added to the biological apatite. Fluorine can be useful in dental applications. Between about 0.01 M and about 0.1 M of a fluorine additive can be included in the aqueous solution. Suitable fluorine additives include, but are not limited to, fluorine salts, which can be prepared from alkali and/or alkaline metal ions, including but not limited to sodium fluoride, calcium fluoride, potassium fluoride, combinations thereof, or acids such as hydrofluoric acid and combinations thereof. Other suitable additives include sodium, magnesium, potassium, chlorine, iodine, lithium, citrate ions, and combinations thereof. The aqueous solution can be deionized water, phosphate buffer, hepes buffer, goods buffers (which can be tunes to an appropriate or desired pH range), tris buffer, SBF, or the like. The type of aqueous solution can affect the final mineral property. For example, when a tris buffer is used as the aqueous solution (without any additives), the resulting apatite is not substituted. When SBF is used, the resulting apatite can be substituted with the ionic component of the solution, which can be sodium, magnesium, potassium, chlorine, or combinations thereof. The final composition comprising the ions, for example calcium or phosphate ions, can result in larger crystals.

The biological apatite can further include an enhancer. The enhancer can be a protein, a cell, a drug, an antibody, a growth factor, a cell, and combinations thereof. Between about 0.001 mg and about 1.0 mg grams of the enhancer can be added to the biological apatite. The enhancers can be added to the biological apatite by soaking the mineralized matrices in the enhancer, or by seeding the enhancer by putting a concentrated cell suspension on top of the matrix and allowing the cells to adhere and proliferate on the matrix. Combinations of these method can also be used. The biological apatite can also have at least one property selected from the group consisting of bioactive, osteoinductive, osteoconductive and combinations thereof.

An aspect of the invention is a method of using a biological apatite. The apatite can be used with bone grafts, fillers, dental cavities, 3-D cultures, cell culture systems, cell scaffolds, regenerative templates, bio-ink, or composite ink. The apatite can also be applied to composite materials for tuning biological interactions or to the interface of non-biological systems to prevent biofouling of surfaces. The apatites can also be applied as a coating to a surface exposed to marine environments. For example, the coating can prevent the formation of deposits (for example barnacles) on surfaces of ship hulls.

Another advantage is that the hydrogel of the present invention can be implemented as a medical device.

Figure 1B:
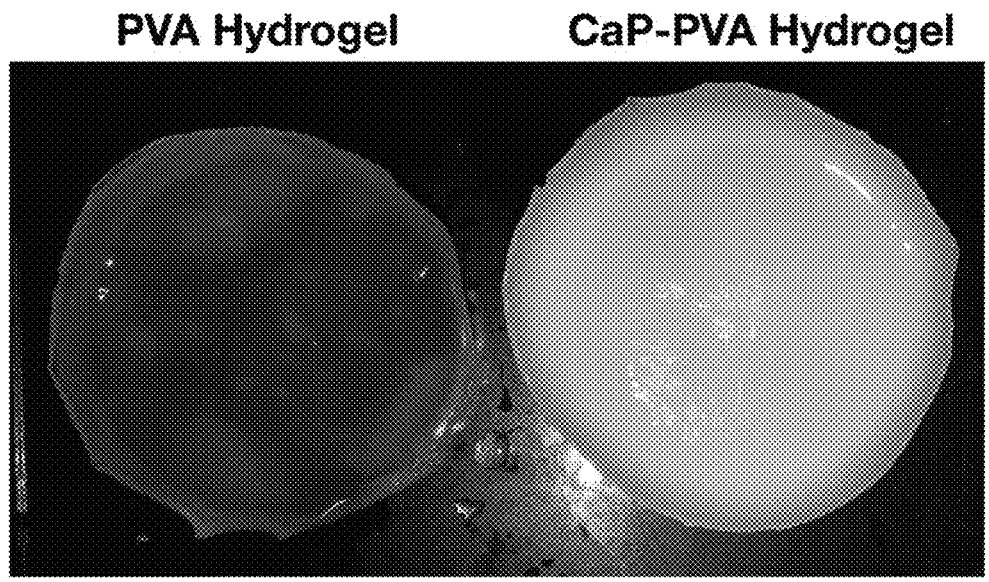
FIG. 1B illustrates photographs of a PVA hydrogel (left) and a mineralized PVA hydrogel composite (right)

FIG. 1A illustrates a method to prepare a mineralized hydrogel composite material. FIG. 1B depicts photographs of a PVA hydrogel (left) and a mineralized-PVA hydrogel composite (right). Through the manipulation of key reaction variables including reaction pH, CaP stoichiometry, and the ion content of the reaction solution results in successful maturation of the CaP mineral phase within the hydrogel to be in accordance with various biological apatites. The resulting materials can be characterized for the in situ growth of apatite by X-ray diffraction (XRD), infrared (IR) spectroscopy, scanning electron microscopy (SEM) imaging, and in vitro cell studies. This invention can be used to provide tailor materials that mimic the natural composition of bone and dental tissue to serve in the repair and potential regeneration to healthy tissue. The advantage of the technology described facilitates the conversion of CaP into biomimetic apatite within polymeric hydrogel systems through the manipulation CaP ratio, temperature, and pH with a direct application as synthetic graft materials.

EXAMPLES

Figure 6:
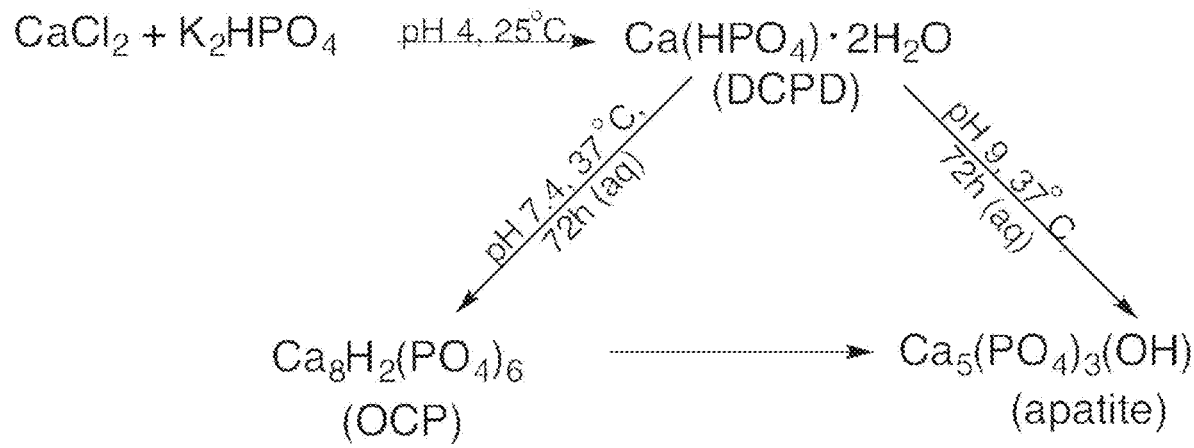
FIG. 6 illustrates the pH responsive hydrolysis pathway of the invention.

Rather than attempting to directly synthesis apatite within a polymeric hydrogel, the present method is inspired by natural mineralization processes where the CaP polymorph is matured to apatite within the polymeric hydrogel matrix. Apatite-PVA hydrogels are prepared by initially precipitating DCPD into an aqueous solution of PVA as illustrated in FIG. 1. The DCPD-PVA solution is physically crosslinked using a cyclic freezing/thawing method forming hydrogels which are insoluble in water and instead undergo slow degradation. This feature of PVA has led to its preferred use in the preparation of biomaterials intended for regenerative applications. The DCPD-PVA hydrogels are then matured to apatite by immersing in aqueous solutions with the pH varied between 7.4 and 9, according to the scheme set forth in FIG. 6. FIG. 6 illustrates the pH responsive hydrolysis pathway of the present invention.

Biomineralization of hard tissues is a stepwise process beginning with the initial deposition of amorphous calcium phosphate (ACP) on the collagen fibrils, followed by hydrolysis to mature apatite. Extensive investigations of calcium phosphate polymorph chemistry indicate that under physiological conditions, metastable polymorphs including ACP, dicalcium phosphate dihydrate (DCPD), and octacalcium phosphate (OCP) transform to apatite. In vitro models for examining the biomineralization process have extensively investigated the transformation pathways of precursors and indicate that apatite formation adheres to Ostwald's law of stages. The pathway in FIG. 6 illustrates the hydrolysis of DCPD to apatite governed by pH-responsive processes, where under physiological mimetic conditions the formation of OCP as a transition state is observed, but as the alkalinity of the solution is increased the direct conversion to apatite is observed. Apatite products resulting from DCPD hydrolysis can be substituted with carbonate or fluoride ions by the incorporation of the substituting ions into the aqueous hydrolysis solution, resulting in the selective synthesis of bone and dental mimetic calcium phosphate polymorphs.

Preparation of Hydrogel

PVA (M.W. 30,000-50,000 Da), sodium hydroxide, calcium chloride dihydrate, hydroxyapatite, and Tris buffer were obtained from Sigma Aldrich (St. Louis, Mo.). Dibasic potassium phosphate was obtained from Fisher Scientific (Waltham, Mass.).

DCPD-PVA composite hydrogels were prepared by the direct precipitation of DCPD in an acidic (pH 3.5) aqueous polymeric solution according to FIG. 1. A 10% PVA solution was prepared by adding about 5 grams PVA directly to about 45 mL of Millipore water (18MΩ) at about 75° C. under vigorous stirring until the polymer was fully solvated. Once dissolved, about 6.25 mL of a 2M $CaCl_2$ stock solution was added to the reaction solution. Next, under continuously stirred conditions, an appropriated amount of $K_2HPO_4$ was added drop-wise to the calcium-containing polymer solution to give a final Ca/P ratio of 1.67. Upon addition of the phosphate solution, a white precipitate was immediately observed. The pH of the PVA solution was maintained at about 3.5. The solution was then poured into 35 mm circular molds for crosslinking. Physical crosslinking was achieved by freezing the materials at −20° C. for 24 hours with subsequent thawing at room temperature for a total of 5 freeze/thaw cycles.

Hydrolysis of DCPD to Apatite

Hydrolysis of the precipitated DCPD was facilitated by the immersion of the crosslinked DCPD-PVA hydrogel in aqueous solutions of Tris buffer adjusted to pH 7.4 or pH 9 maintained at about 37° C. for about 72 hrs. Ionic substitution of the apatite lattice was achieved by preparing Tris buffer solutions with added 0.1M sodium bicarbonate and 0.025M sodium fluoride. The pH of the reaction solution was monitored for the duration of the reaction. Deviations in pH as a result of hydrolysis were corrected by the addition of 1M sodium hydroxide. The reaction was determined to reach completion when the reaction solution pH remained constant over about a 24-hour period. Following hydrolysis, the apatite-PVA hydrogels were removed from the reaction solution and dehydrated by exposure to ambient conditions.

Characterization of Precipitated Mineral Phase

The composition of the mineral phase formed within the polymer matrix was examined by Fourier Transform Infrared Spectroscopy (FTIR, Nexus 470 e.s.p.) over the range of 550-4000 using an attenuated total reflectance accessory (Specac, Golden Gate) equipped with a diamond crystal. Powder X-Ray diffraction (pXRD, Phillips X'pert) was used to analyze the crystalline phase of the calcium phosphate precipitates within the polymeric matrix. Dehydrated polymer samples were analyzed over the 2 theta range of 20 to 60° with a step size of 0.02 degrees with Cu-K radiation ($\lambda$=1.54060 Å). The materials were visualized with the use of a scanning electron microscope (SEM, JEOL 7000) equipped with energy dispersive X-ray (EDX) analysis. Each of the polymeric materials examined were sputtered with gold and placed in an evacuated chamber. The accelerating voltage of the instrument was set to 20 kV.

Cellular Attachment to Hydrogel Surfaces 50,000 MC3T3-E1 subclone 4 murine preosteoblast cells were seeded onto hydrogel scaffolds of PVA and apatite-PVA presoaked in Dulbecco's Minimal Essential Media with about 1 g/L glucose (DMEM low glucose). The scaffolds were cylindrical materials with an about 5 mm radius and about 3 mm height, with a surface area of about 251 $mm^2$. The samples (repeated in triplicate) were cultured in 24-well plates in about 0.4 mL of DMEM-LG+10% fetal bovine serum in an about 37° C. humidified incubator. About 48 hours after cell seeding, the cells on the scaffolds were stained with fluorescein diacetate (1.5 mg/mL DMSO) (live) and ethidium bromide (1 mg/mL PBS) (dead) cells. The scaffolds were imaged on a Nikon Eclipse TE2000-S microscope a white light source (X-Cite Series Q, Lumen Dynamics) at 20× magnification.

Characterization of Mineralized Hydrogels

Figure 2:
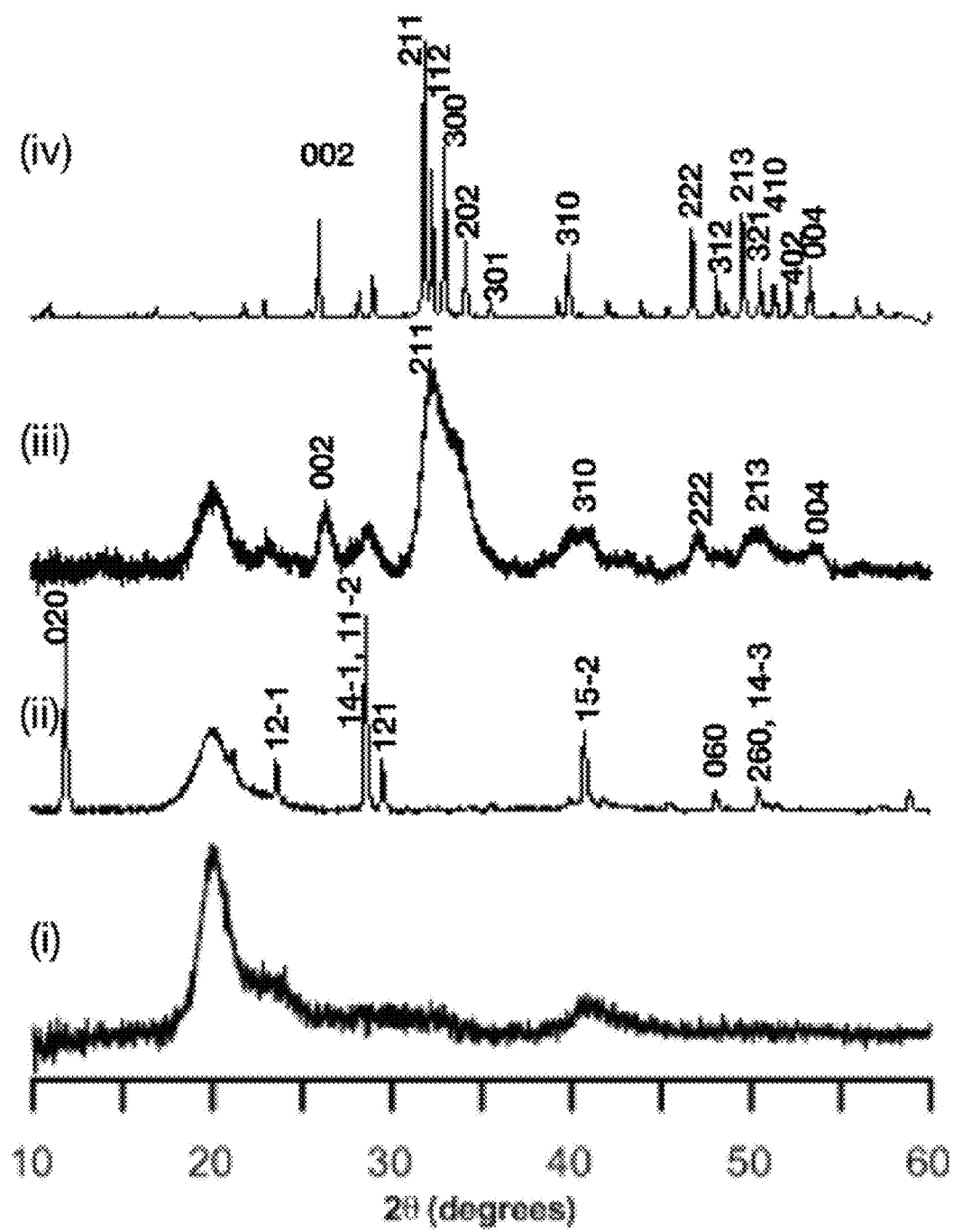
FIG. 2 illustrates a characterization of mineralized-PVA by powder x-ray diffraction, and illustrates patterns of (i) PVA hydrogel, (ii) initial DCPD-PVA hydrogel, (iii) apatite-PVA hydrolyzed at a particular condition, and (iv) hydroxyapatite.

FIG. 2 illustrates a characterization of mineralized-PVA hydrogels by powder x-ray diffraction (pXRD). FIG. 2 includes pXRDs for a PVA hydrogel (i); an initial DCPD-PVA hydrogel (ii); an apatite-PVA hydrolyzed at pH 7.4, at a temperature of about 37° C., for about 72 hours (iii); and hydroxyapatite (iv). The PVA matrix exhibited a broad diffraction peak associated with PVA at 20 degrees. The initially precipitated calcium phosphate polymorph in the PVA matrix (FIG. 2(ii)) resulted in the appearance of a crystalline structure with diffraction peaks at 11, 21, 29, 30, and 40 degrees. These peaks do not correlate with the formation of apatite, but rather through comparison with reported patterns of polymorphs, the initially formed precipitate was determined to correspond with the formation of DCPD. Immersion of the DCPD-PVA hydrogel in the aqueous buffer resulted in the transformation of the diffraction pattern (FIG. 2(iii)). The diffraction patterns were found to exhibit key peaks at 26, 31, and a triplicate cluster between 48-52 degrees. In comparison to the diffraction pattern of hydroxyapatite (FIG. 2(iv)), the resulting product was determined to be consistent with the formation of poorly crystalline apatite.

Figure 3:
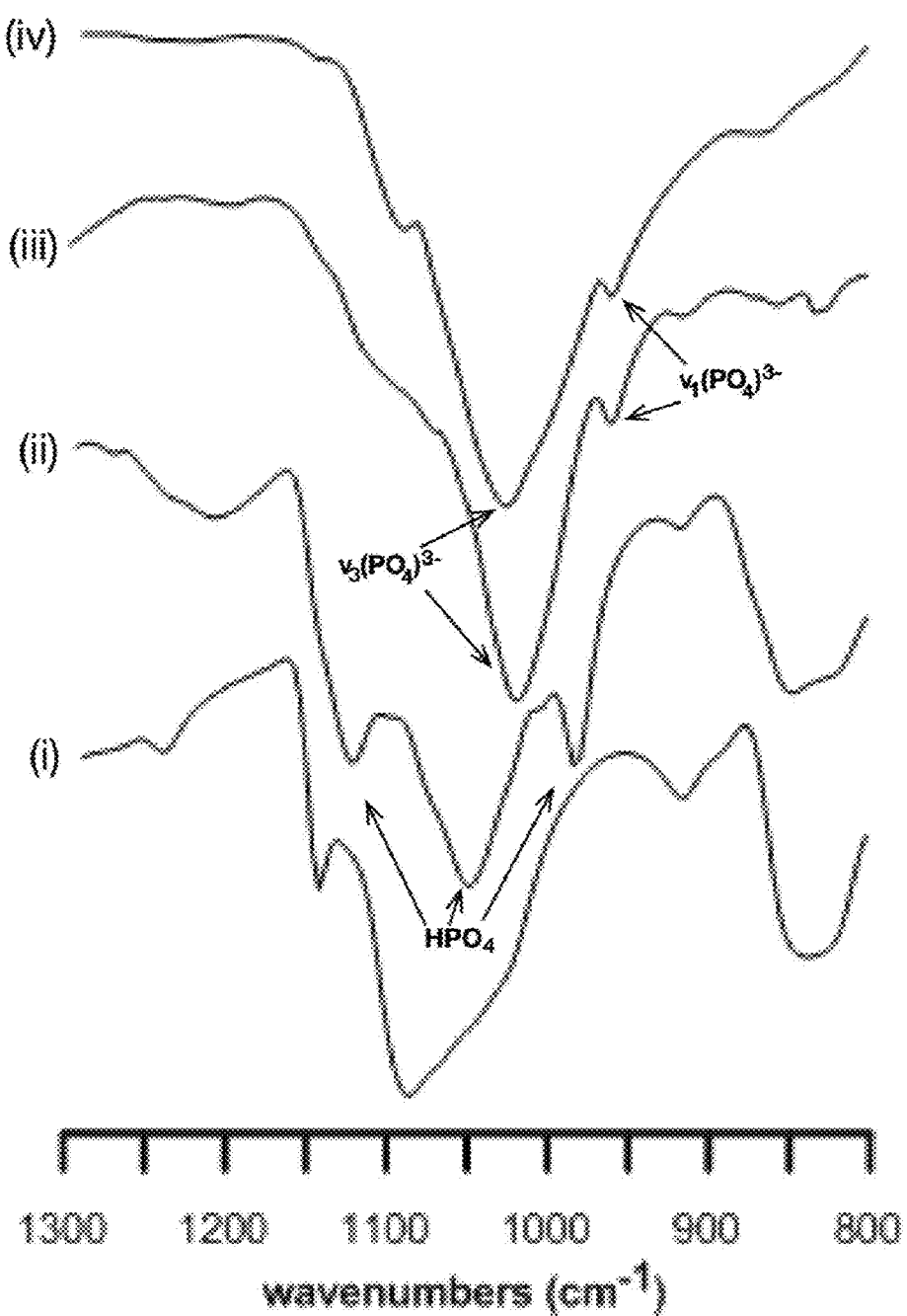
FIG. 3 illustrates an attenuated total reflectance infrared spectra of mineralized polyvinyl alcohol (PVA) materials of the POO stretch region with spectra for (i) PVA hydrogel, (ii) initial DCPD-PVA, (iii) apatite-PVA at pH 7.4, and (iv) hydroxyapatite.
Figure 8:
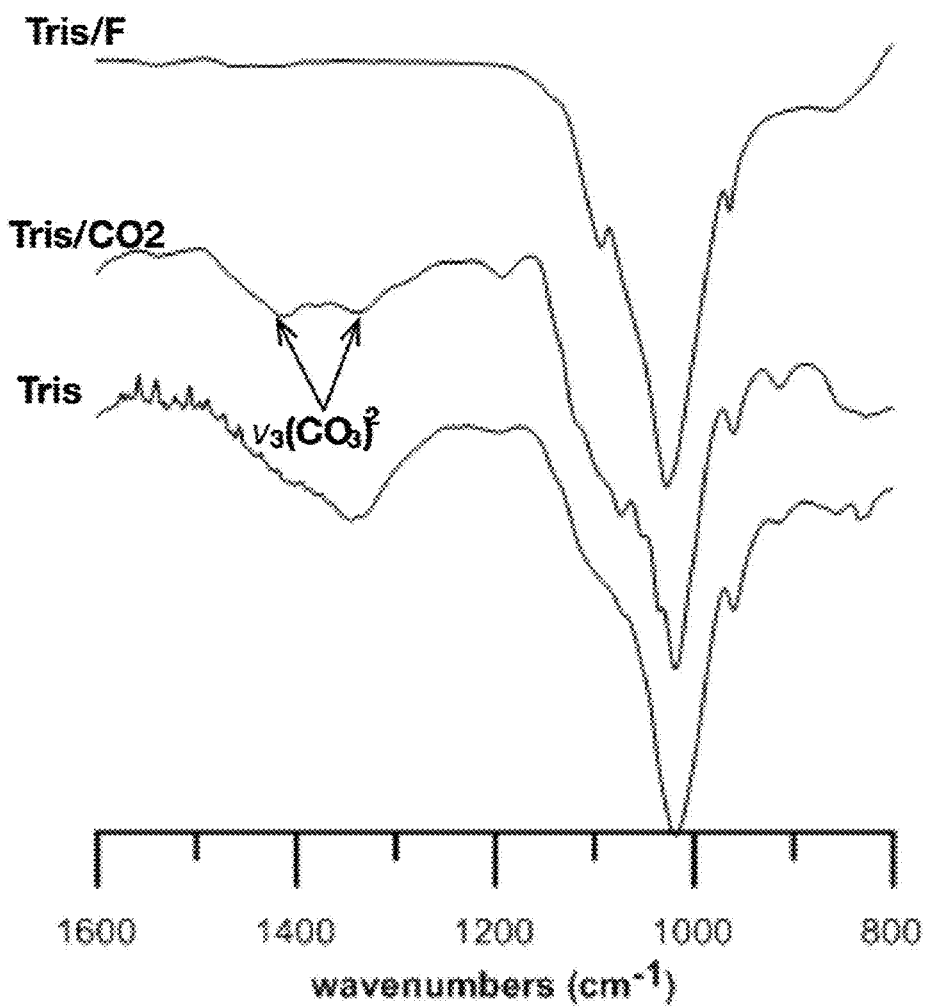
FIG. 8 illustrates the IR spectra of the apatite-PVA hydrogels synthesized in Tris buffer without additives.

FIG. 3 depicts an attenuated total reflectance infrared (ATR-IR) spectra of mineralized polyvinyl alcohol (PVA) polymeric substrates of the P-O stretch region. In the IR spectra of calcium phosphate materials, the region of interest is the P-O stretch between 850-1200 $cm^{-1}$ as illustrated in FIG. 8. The PVA spectra contained three significant peaks in this region of interest, at 910 $cm^{-1}$, 1042 $cm^{-1}$, and 1140 $cm^{-1}$. Examination of mineralized hydrogels indicated that the absorbance features associated with PVA were not detected. The IR spectra of the initially precipitated mineral phase contained four key peaks at 983, 1003, 1053, and 1120 $cm^{-1}$ (FIG. 3(ii)). A comparison with synthetic hydroxyapatite (FIG. 3(iv)) indicates a lack of relation, but there is a correlation with previously reported IR values of DPCD. Hydrolysis of the DCPD-PVA hydrogels at pH 7.4 resulted in the transformation of the spectra to correlate with synthetic hydroxyapatite. A sharp single peak at 1026 $cm^{-1}$ and shoulder at 960 $cm^{-1}$ were present in the hydrolyzed products (FIG. 3(iii)). These peaks are distinctly related to hydroxyapatite spectra and do not have any correlation with the prior phase. Thus, the formation of DCPD within a hydrogel network and its subsequent hydrolysis to apatite was demonstrated.

The mineralized hydrogels formed initially incorporated DCPD and slowly hydrolyzed to apatite. The transformation of DCPD to apatite is a hallmark reaction in calcium phosphate chemistry, where it is understood that apatite is the most stable polymorph which forms from DCPD as a result of Ostwald's ripening. The progressive maturation of bone mineral is known to be in accordance with this model, and furthermore, it is known that the composition of biomineralized apatite is subject to the composition of surrounding body fluid.

Selective Tuning Apatite Composition Morphology and Composition

Apatite Morphology is pH Dependent

Figure 4:
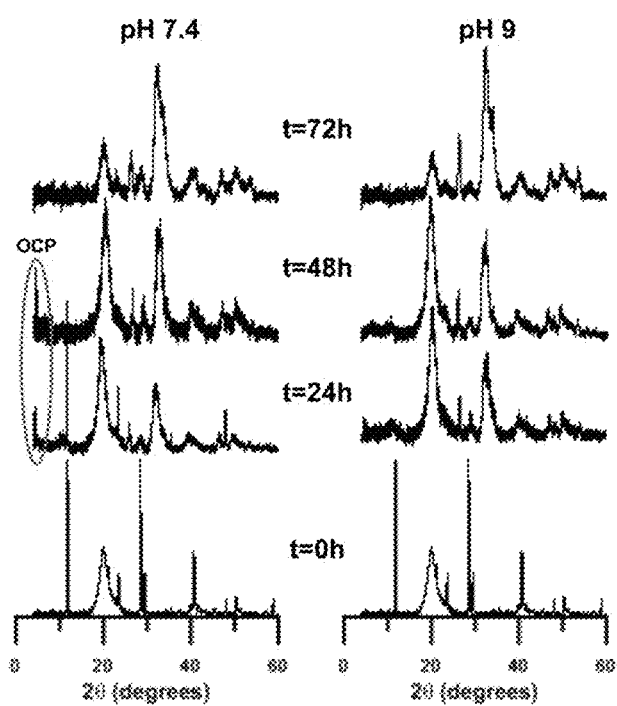
FIG. 4 illustrates powder x-ray diffraction patters of mineralized-PVA hydrogels at 24 hour intervals when immersed in an aqueous solution at pH of 7.4 and 9.

FIGS. 4 and 5A-C illustrate the calcium phosphate transformation within PVA hydrogels by aqueous hydrolysis. FIG. 4 illustrates pXRD patterns of mineralized-PVA hydrogels at 24 hour intervals when immersed in an aqueous solution at a pH of 7.4 or 9, respectively. After immersion for 72 hours at pH 7.4 and 9, respectively, the product was determined to be apatite. Examination of the incorporated calcium phosphate particles after 24 hours indicated an immediate transformation of DCPD to apatite. The sustained presence of peaks associated with DCPD indicates incomplete transformation to apatite. Comparison of the 24 hour and 48-hour diffraction patterns at each of the investigated pH values indicates that only at pH 7.4 was an additional peak at 4 degrees detected. This peak is not associated with either DCPD or apatite and is instead attributed to the formation of OCP as an intermediate phase. The diffraction patterns of OCP and apatite are very similar and the peak at 4 degrees is commonly used as a diagnostic handle for distinguishing between the formation of OCP and apatite. The ultimate disappearance of this peak after 72 hours indicates the successful transformation to apatite. Therefore, the hydrolysis of DCPD to apatite at pH 7.4 is determined to occur with OCP as an intermediate phase. In contrast, at pH 9 the direct hydrolysis of DCPD to apatite without an intermediate phase occurs. These results are summarized in FIG. 6.

Figure 5A:
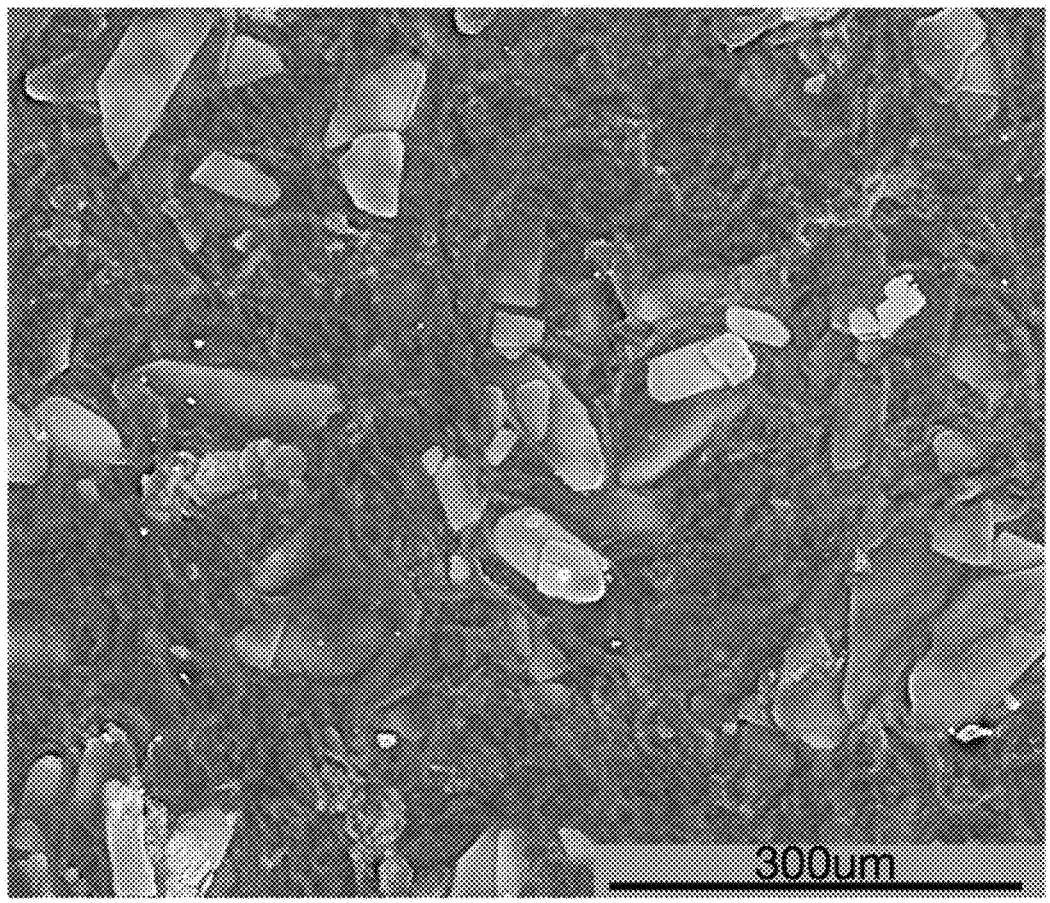
FIG. 5A illustrates a SEM image of calcium phosphate mineralization of the PVA matrix initially.
Figure 5B:
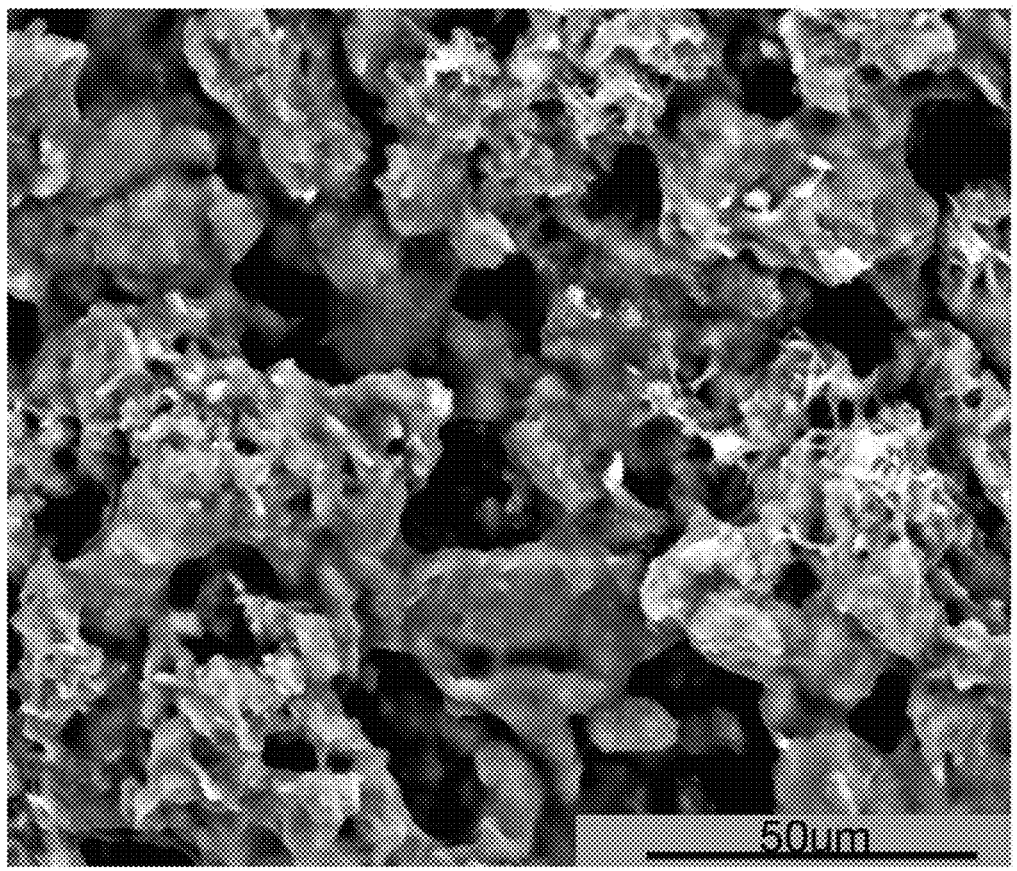
FIG. 5B illustrates a SEM image of calcium phosphate mineralization of the PVA matrix after 72 hours at a pH of 7.4.
Figure 5C:
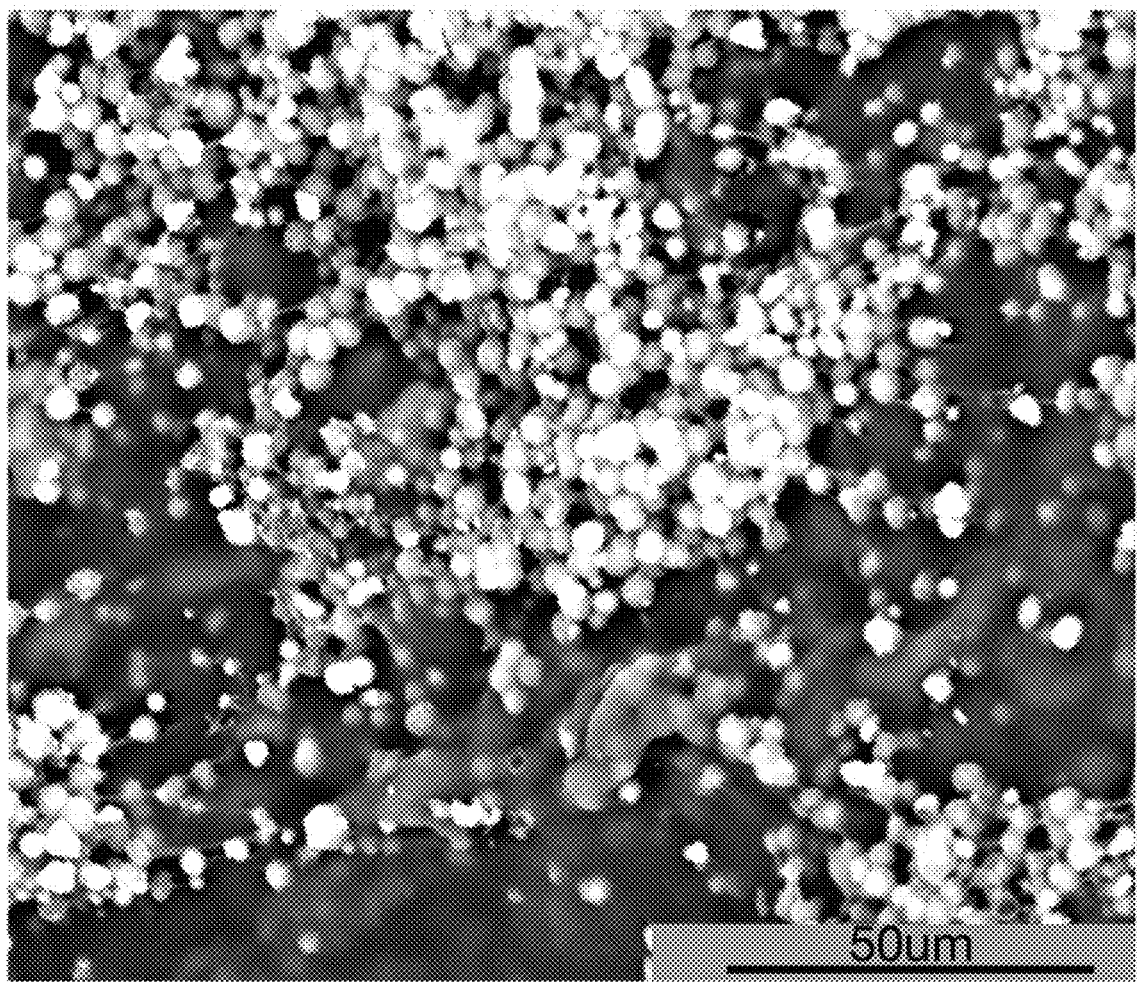
FIG. 5C illustrates a SEM image of calcium phosphate mineralization of the PVA matrix after 72 hours at a pH of 9.

FIGS. 5A-C illustrates SEM images of the calcium phosphate transformation within PVA hydrogels by aqueous hydrolysis. FIG. 5A illustrates a SEM image of calcium phosphate-PVA at an initial time. FIG. 5B illustrates calcium phosphate-PVA after soaking in an aqueous solution for 72 hours at pH 7.4. FIG. 5C illustrates a calcium phosphate-PVA after soaking in an aqueous solution for 72 hours at a pH of 9. The initially precipitated DCPD particles exhibited a plate-like morphology and were randomly dispersed throughout the polymeric matrix (FIG. 5A). Immersion of DCPD-PVA materials in Tris buffer at pH 7.4, 37° C. (FIG. 5B) resulted in the transformation to apatite particles exhibiting an interconnected network. Hydrolysis at pH 9 (FIG. 5C) resulted in the formation of individual spherical apatite particles. The variation in apatite particle morphology is likely a result of the formation pathway of DCPD to apatite.

The transformation pathway of DCPD to apatite was determined to be pH dependent (illustrated in FIG. 6) and resulted in deviations in the resulting morphology of the apatite particles. Tuning the hydrolysis solution pH to 7.4 resulted in the formation of OCP as an intermediate before conversion to apatite was observed. These results are consistent with the proposed mechanisms of biomineralized apatite. In contrast, increasing the pH to 9 resulted in the direct transformation to apatite. The pH dependent hydrolysis pathway resulted in variations in the particle morphology, where interconnected networks are formed at pH 7.4 compared with individual spherical particles when the pH was increased to 9. At low pH, the apatite particles formed are pseudomorphs of the OCP precursor phase. This intermediate OCP phase arises because the apatite crystal formation is slower than OCP formation. In contrast, at pH 9 the apatite product is the favored phase and is readily formed without competition from OCP. The apatite phase is not a pseudomorph of DCPD since it is formed from the dissolution of DCPD and recrystallization to the apatite product. In summary, by selectively tuning the pH of the immersion buffer, hydrogels can be mineralized with apatite according to biomimetic synthetic pathways.

Preparation of Carbonate and Fluoride Substituted Apatite

Biological apatites deviate significantly from hydroxyapatite based on their poor crystallinities and high degrees of lattice substitutions. Biological apatites are calcium deficient apatites substituted with numerous ions including $CO_3^{2-}$, $Na^+$, $Mg^{2+}$, $K^+$, and $F^-$. The differences between bone and dental minerals are a result of doping the lattice structure with different ions. For example, while bones are principally carbonate substituted, in teeth the $F^-$ content is at a maximum on the surface of enamel, and it decreases progressing into dentin and further to bone. Inspired by biological formation conditions, carbonate and fluoride ions were added to the hydrolysis buffer to selectively form carbonate or fluoride substituted apatite.

Figure 7:
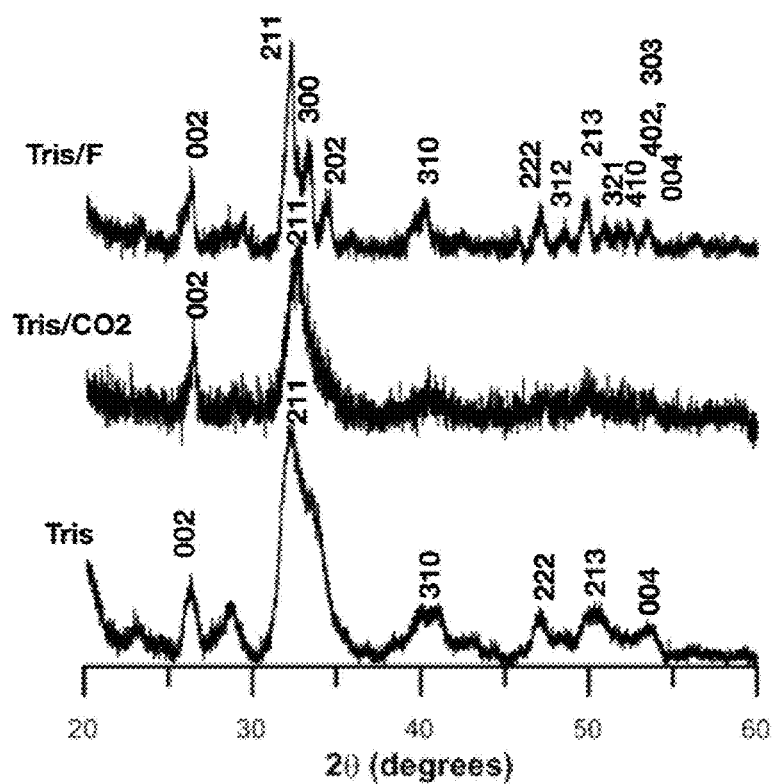
FIG. 7 illustrates XRD patterns of mineralized hydrogels hydrolyzed in the presence of carbonate or fluoride ions.

FIG. 7 illustrates XRD patterns of mineralized hydrogels hydrolyzed in the presence of carbonate or fluoride ions. These XRD patterns were compared to the pattern of the apatite product without solution additives. Apatite remained the final mineral phase formed even in the presence of solution additives. The addition of carbonate to the hydrolysis solution resulted in the formation of a poorly crystalline apatite product, consistent with the results observed for the composite materials hydrolyzed in the additive-free Tris buffer. The presence of carbonate ions in biomineralized apatites can be attributed to the observed low crystallinities of bone mineral.

In contrast, the hydrolysis of the DCPD in a fluoride solution resulted in the formation of a highly crystalline apatite product, with the apatite peaks clearly resolved and the corresponding crystal faces easily identified (FIG. 7). Substitution of the apatite lattice with fluoride ions is known to decrease the disorder of the hydroxide backbone even at low temperatures, resulting in an increase in the observed crystallinity of the apatite product. The resulting apatite pattern when matured in the presence of fluoride matched the pattern observed for hydroxyapatite synthesized at high temperature (FIG. 2(iv)). At a fluoride concentration of 0.025 M, the exclusive formation of apatite as the product was determined. However, increasing the fluoride concentration to about 0.075 M and 0.1 M, respectively, resulted in the formation of apatite and $CaF_2$ as a side product based on the presence of $CaF_2$ diffraction peaks in the XRD pattern (data not shown).

The incorporation of carbonate and fluoride ions into the apatite lattices was verified by FTIR-spectroscopy and EDX analysis, respectively. FIG. 8 illustrates the IR spectra of the apatite-PVA hydrogels synthesized in Tris buffer without additives. These spectra are compared to those synthesized in Tris buffer with added carbonate or fluoride ions. Each of the resulting spectra were similar in appearance regarding the P-O stretch. However, the apatite product hydrolyzed in the carbonate solution resulted in the formation of doublet peaks illustrated in FIG. 8, not present when hydrolyzed in Tris buffer alone or with added fluoride ions. The observed peaks in the carbonate substitution are consistent with the ☐3(CO$_3$)$_2$— stretch previously observed in CO$_3$-apatite.

Figure 9A:
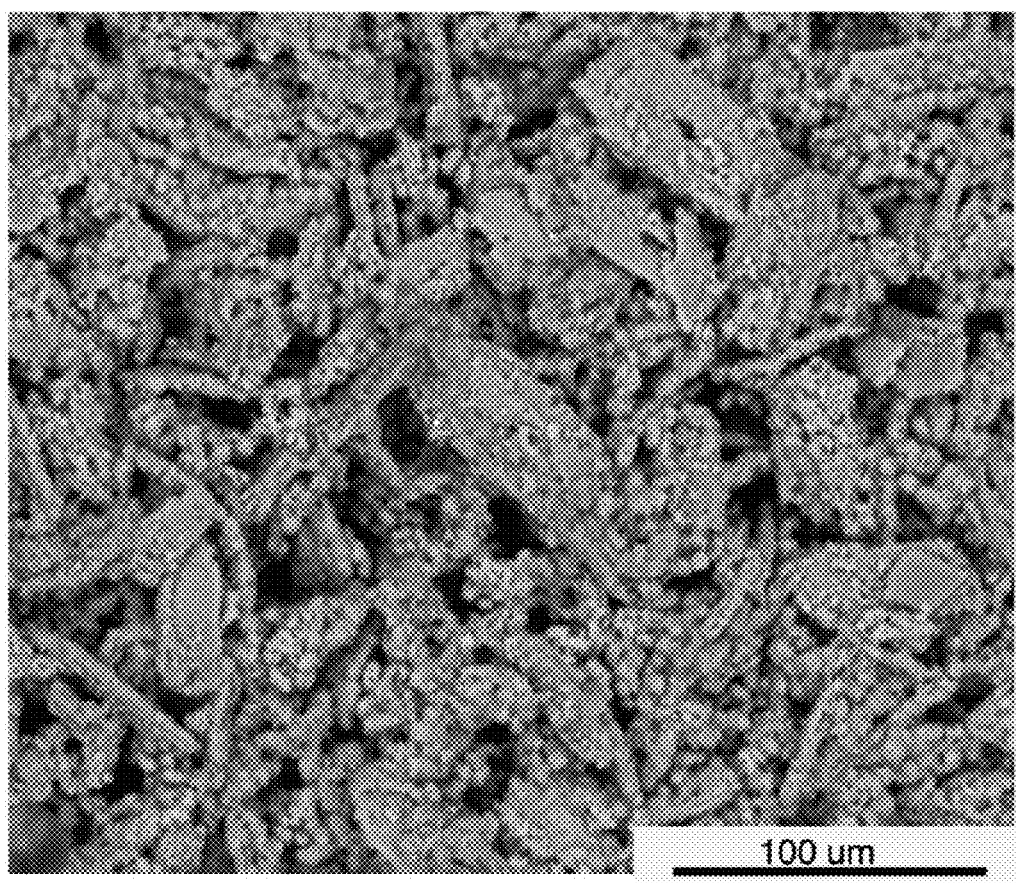
FIG. 9A depicts SEM-EDX analysis for Tris/F materials.
Figure 9B:
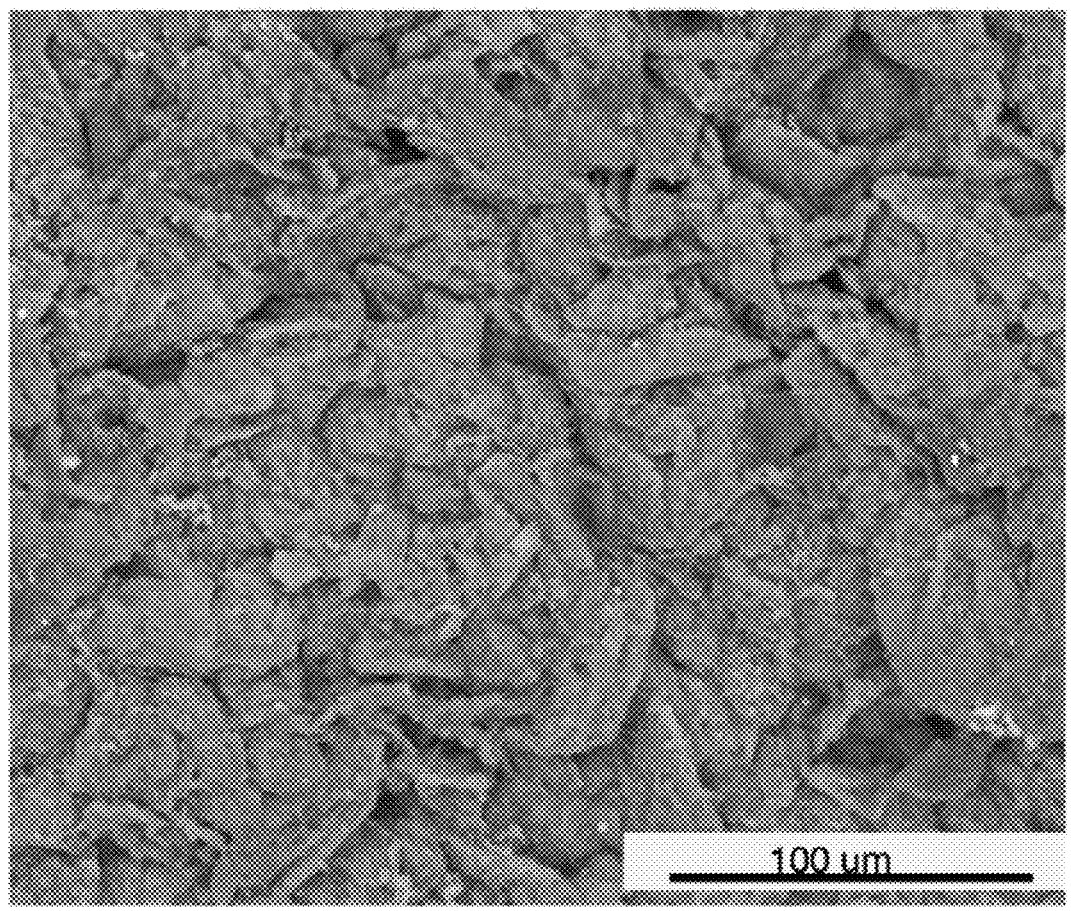
FIG. 9B depicts SEM-EDX analysis for Tris/$CO_2$ materials.
Figure 10:
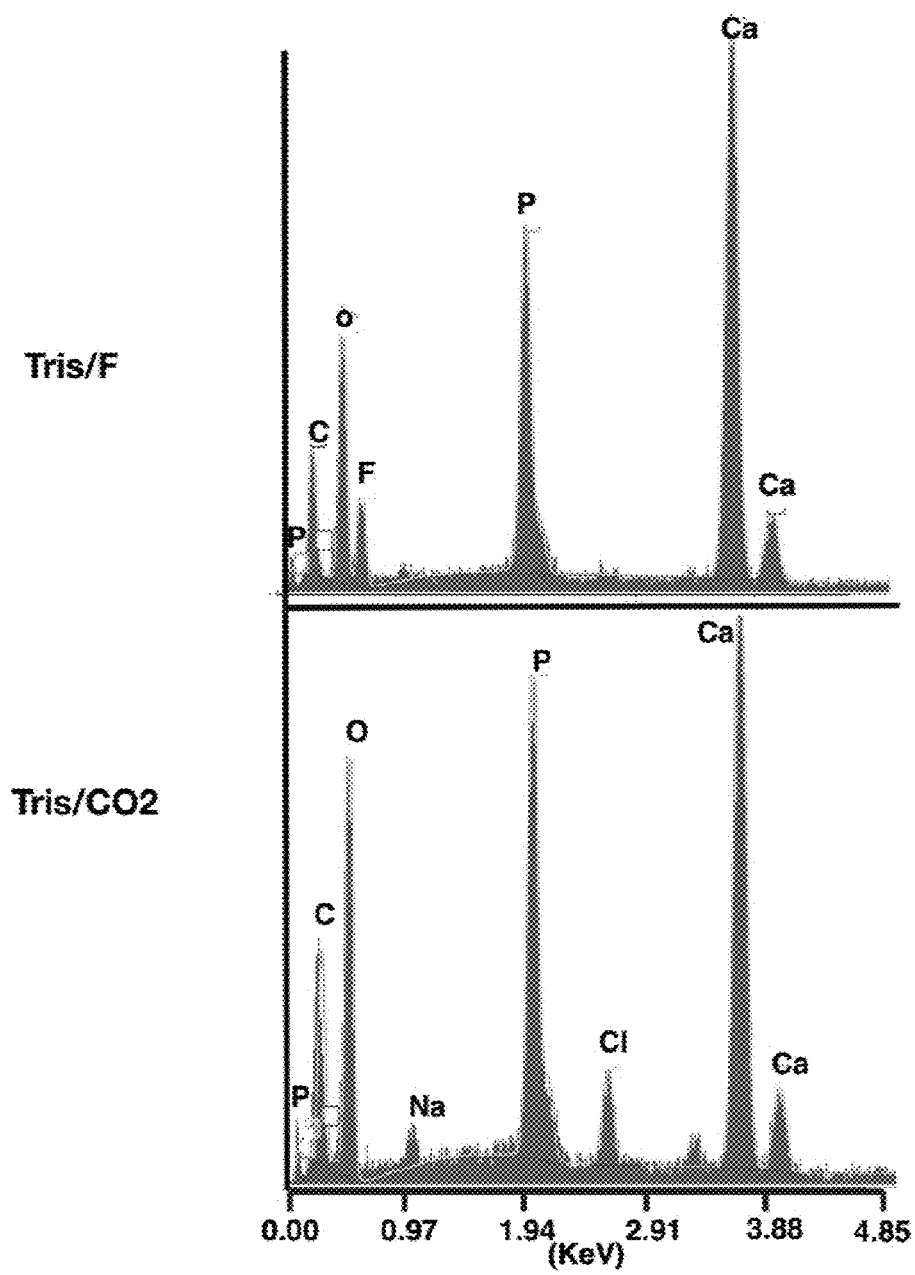
FIG. 10 depicts SEM-EDX analysis for Tris/F and Tris/$CO_2$ materials corresponding to the SEM images in FIGS. 9A and 9B.

FIGS. 9A, 9B and 10 depict SEM-EDX analysis for Tris/F and Tris/CO$_2$ materials. The SEM-EDX images were used to visualize the composite materials and determine the elemental composition of the apatite product formed after hydrolysis in the fluoride-containing solution, compared to the apatite product formed in Tris buffer without additives. A peak associated with F in the EDX spectra of the material hydrolyzed in the fluoride-containing solution can be observed, whereas the spectra of apatite formed in Tris buffer without additives did not have this peak (FIGS. 9A, 9B and 10). These results indicate that the selective incorporation of ionic dopants in the apatite lattice is facilitated by their inclusion in the hydrolysis buffer that is used to transform the initially incorporated DCPD polymorph to apatite.

Cellular Activity of Mineralized Hydrogels

Improvements in the bioactivity of synthetic hard tissue grafts can be obtained via the incorporation of substituted apatite that closely resemble the naturally mineralized tissue. A significant limitation to testing this hypothesis to date has been a lack of methodology for the pre-programming of a mineralization reaction to yield a desired product for a specific application. The present invention demonstrates the development of a method for the controlled in situ mineralization of a synthetic hydrogel with an apatite product that can be selectively tuned, and which mimics biomineralization processes.

Figure 11A:
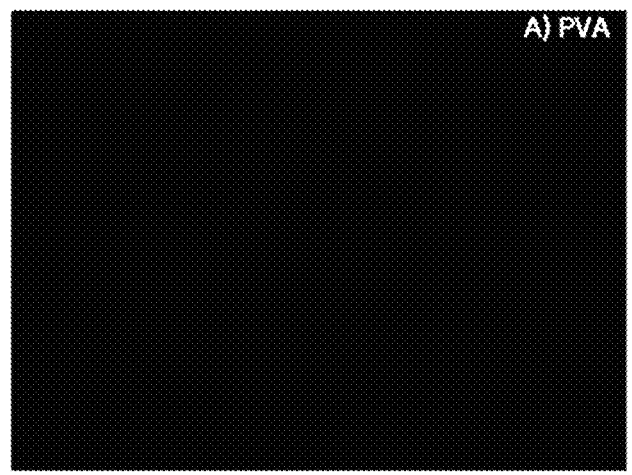
FIG. 11A depicts PVA hydrogel where cells did not adhere to the surface of the hydrogel.
Figure 11B:
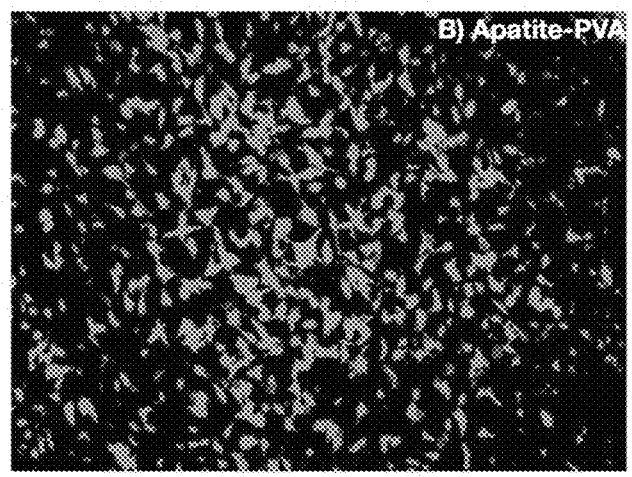
FIG. 11B depicts an apatite-PVA hydrogel with cells adhered to the hydrogel.

MC3T3 preosteoblast cells were seeded on PVA and apatite-PVA hydrogels and the cell attachment examined after 24 hrs. FIG. 11A illustrates PVA hydrogel where cells did not adhere to the surface of the hydrogel. Live (green)/dead (red) staining of the cells indicated that cells were not able to adhere to the surface of the PVA-only hydrogels (as illustrated in FIG. 11A). In contrast, cells were firmly attached and spread onto the surface of the apatite-PVA hydrogels with high cell viability (as illustrated in FIG. 11B).

Ranges have been discussed and used within the forgoing description. One skilled in the art would understand that any sub-range within the stated range would be suitable, as would any number within the broad range, without deviating from the invention.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed:

1. A method to form a tunable biological apatite hydrogel composite, consisting of:
    preparing a polymer hydrogel;
    mixing a calcium source, a phosphate source and the polymer hydrogel to produce a slurry;
    crosslinking the slurry to produce a tunable polymer comprising a dicalcium phosphate dihydrate (DCPD) in the hydrogel; and
    soaking the polymer comprising the DCPD in the hydrogel in an aqueous solution to tune the DCPD in the hydrogel for an application to produce the biological apatite hydrogel composite, wherein the aqueous solution is selected from the group consisting of a deionized water, a phosphate buffer, a hepes buffer, a goods buffer, a tris buffer, a simulated body fluid, and wherein the aqueous solution comprises between about 0.0042 and about 0.1M of an additive selected from the group consisting of a bicarbonate, a fluoride, a sodium, a potassium, a chloride, a magnesium, a citrate ion, and combinations thereof.

2. The method of claim 1, wherein the polymer hydrogel is at least one of a polyvinyl alcohol, a collagen, a methyl acrylate, a polyethylene glycol, a chitosan, an alginate, dextran, hyaluronic acid, a gelatin or a cellulose.

3. The method of claim 1, wherein a ratio of the calcium source to the phosphate source is between about 1:0.5 to 1:2.

4. The method of claim 1, wherein between about 2 to about 20 wt. % polymer is added to the water.

5. The method of claim 1, wherein the calcium source is a selected from the group consisting of calcium chloride, calcium nitrate, calcium carbonate, calcium fluoride, and combinations thereof.

6. The method of claim 1, wherein the phosphate source is a dibasic phosphate compound.

7. The method of claim 6, wherein the dibasic phosphate compound is selected from the group consisting of K$_2$HPO$_4$, ammonium phosphate, phosphoric acid and combinations thereof.

8. The method of claim 1, wherein a temperature of the method is between about 20° C. and about 40° C.

9. The method of claim 1, wherein a pH of the slurry is between about 3.5 and about 5.

10. The method of claim 1, wherein a pH of the slurry is adjusted to between about 3.5 and about 5 with a strong acid selected from the group consisting of hydrochloric acid, nitric acid, sulphuric acid, and combinations thereof.

11. The method of claim 1, wherein the polymer comprises polyvinyl alcohol, and wherein the crosslinking comprises thermal cycling the polymer between a temperature to freeze the biological apatite and a temperature to thaw the biological apatite, wherein the biological apatite is cycled at least four times.

12. The method of claim 1, wherein the aqueous solution is at a pH of between about 6.5 to about 7.4 to form a mineral phase biological apatite comprising octacalcium phosphate.

13. The method of claim 12, wherein the octacalcium phosphate is converted to a second material comprising apatite.

14. The method of claim 11, wherein the temperature to freeze is about −80° C. and wherein the temperature to thaw is about 20° C.

15. The method of claim 11, wherein the thermal cycling further comprising maintaining the polymer at the temperature to freeze for between about 4 hours and about 24 hours, and maintaining the polymer at the temperature to thaw for between about 4 hours and about 24 hours.

16. The method of claim 1, wherein the crosslinking comprises photocrosslinking.

17. The method of claim 1, wherein the calcium source comprises calcium and a counterion.

18. The method of claim 1, wherein the phosphate source comprises phosphate and a counterion.

\* \* \* \* \*